(12) United States Patent
Bertagnoli et al.

(10) Patent No.: US 10,583,014 B2
(45) Date of Patent: *Mar. 10, 2020

(54) INTERVERTEBRAL IMPLANT WITH KEEL

(71) Applicant: CENTINEL SPINE, LLC, New York, NY (US)

(72) Inventors: Rudolf Bertagnoli, Wein (AT); Shaun Hanson, West Chester, PA (US); Joern Richter, Oberdorf (CH); John Paul Furda, New Port Richey, FL (US); Fabian Haller, Basel (CH); David Gerber, West Chester, PA (US); Roger Berger, Oberdorf (CH); Stefanie Kaufmann, Hilzingen (DE)

(73) Assignee: Centinel Spine, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/888,505

(22) Filed: Feb. 5, 2018

(65) Prior Publication Data
US 2018/0153705 A1    Jun. 7, 2018

Related U.S. Application Data

(63) Continuation of application No. 14/643,287, filed on Mar. 10, 2015, now Pat. No. 9,387,086, which is a
(Continued)

(51) Int. Cl.
*A61F 2/44* (2006.01)
*A61B 17/14* (2006.01)
(Continued)

(52) U.S. Cl.
CPC ............ *A61F 2/442* (2013.01); *A61B 17/144* (2016.11); *A61B 17/15* (2013.01);
(Continued)

(58) Field of Classification Search
CPC .......... A61F 2/442; A61F 2/44; A61F 2/4425; A61F 2/4684; A61F 2002/30056;
(Continued)

(56) References Cited

U.S. PATENT DOCUMENTS

| 114,816 A | 5/1871 | Hiestand |
| 2,854,981 A | 10/1958 | Morrison |

(Continued)

FOREIGN PATENT DOCUMENTS

| CH | 0624573 | 8/1981 |
| CN | 101027005 | 8/2007 |

(Continued)

OTHER PUBLICATIONS

U.S. Appl. No. 11/185,781, filed Jul. 21, 2005, Marnay et al.
(Continued)

*Primary Examiner* — Pedro Philogene
*Assistant Examiner* — David C Comstock
(74) *Attorney, Agent, or Firm* — Farber LLC

(57) ABSTRACT

An intervertebral implant component of an intervertebral implant includes an outer surface for engaging an adjacent vertebra and an inner surface. A keel extends from the outer surface and is designed to be disposed in a slot provided in the adjacent vertebra. This keel extends in a plane which is non-perpendicular to the outer surface; and preferably there are two of the keels extending from the outer surface which are preferably offset laterally from one another. In another embodiment, an anterior shelf is provided at an anterior end of the outer surface, and this anterior shelf extends vertically away from the inner surface in order to help prevent bone growth from the adjacent vertebra towards the inner surface. Further in accordance with disclosed embodiments, various materials, shapes and forms of construction of the component and/or keel provide various benefits.

25 Claims, 12 Drawing Sheets

Related U.S. Application Data continuation of application No. 12/375,071, filed as application No. PCT/US2007/074218 on Jul. 27, 2007, now Pat. No. 8,998,990.

(60) Provisional application No. 60/832,595, filed on Jul. 24, 2006.

(51) Int. Cl.
  *A61B 17/15* (2006.01)
  *A61B 17/16* (2006.01)
  *A61F 2/46* (2006.01)
  *A61F 2/30* (2006.01)

(52) U.S. Cl.
  CPC ...... *A61B 17/1604* (2013.01); *A61B 17/1671* (2013.01); *A61F 2/44* (2013.01); *A61F 2/4425* (2013.01); *A61F 2/4684* (2013.01); *A61F 2002/30056* (2013.01); *A61F 2002/30112* (2013.01); *A61F 2002/30331* (2013.01); *A61F 2002/30383* (2013.01); *A61F 2002/30448* (2013.01); *A61F 2002/30485* (2013.01); *A61F 2002/30507* (2013.01); *A61F 2002/30576* (2013.01); *A61F 2002/30594* (2013.01); *A61F 2002/30604* (2013.01); *A61F 2002/30677* (2013.01); *A61F 2002/30884* (2013.01); *A61F 2002/30891* (2013.01); *A61F 2002/30894* (2013.01); *A61F 2002/30897* (2013.01); *A61F 2002/30899* (2013.01); *A61F 2002/30901* (2013.01); *A61F 2002/30902* (2013.01); *A61F 2002/30904* (2013.01); *A61F 2002/30932* (2013.01); *A61F 2002/443* (2013.01); *A61F 2002/449* (2013.01); *A61F 2220/005* (2013.01); *A61F 2220/0008* (2013.01); *A61F 2220/0025* (2013.01); *A61F 2220/0033* (2013.01); *A61F 2230/0004* (2013.01); *A61F 2250/0032* (2013.01); *A61F 2310/00023* (2013.01); *A61F 2310/0058* (2013.01); *A61F 2310/0088* (2013.01); *A61F 2310/0097* (2013.01); *A61F 2310/00161* (2013.01); *A61F 2310/00179* (2013.01); *A61F 2310/00449* (2013.01); *A61F 2310/00574* (2013.01); *Y10T 83/9454* (2015.04)

(58) Field of Classification Search
  CPC .. A61F 2002/30112; A61F 2002/30331; A61F 2002/30383; A61F 2002/30448; A61F 2002/30485; A61F 2002/30507; A61F 2002/30576; A61F 2002/30594; A61F 2002/30604; A61F 2002/30677; A61F 2002/30884; A61F 2002/30891; A61F 2002/30894; A61F 2002/30897; A61F 2002/30899; A61F 2002/30901; A61F 2002/30902; A61F 2002/30904; A61F 2002/30932; A61F 2002/443; A61F 2002/449; A61F 2220/0008; A61F 2220/0025; A61F 2220/0033; A61F 2220/005; A61F 2230/0004; A61F 2250/0032; A61F 2310/00161; A61F 2310/00179; A61F 2310/00449; A61F 2310/00574; A61F 2310/0058; A61F 2310/0088; A61F 2310/0097; A61B 17/144; A61B 17/15; A61B 17/1604; A61B 17/1671; Y10T 83/9454
  USPC ..... 623/17.11, 17.14, 17.15, 17.16; 606/279, 606/82, 84, 86 A
  See application file for complete search history.

(56) References Cited

U.S. PATENT DOCUMENTS

| | | |
|---|---|---|
| 3,320,951 A | 5/1967 | Wittebol |
| 3,486,505 A | 12/1969 | Morrison |
| 3,510,883 A | 5/1970 | Cathcart |
| 3,579,829 A | 5/1971 | Sampson |
| 3,740,769 A | 6/1973 | Haboush |
| 3,875,595 A | 4/1975 | Froning |
| 3,889,300 A * | 6/1975 | Smith ............. A61F 2/4202 623/21.18 |
| 3,903,549 A | 9/1975 | Deyerle |
| 3,992,726 A | 11/1976 | Freeman et al. |
| D243,286 S | 2/1977 | Deyerle |
| 4,021,864 A | 5/1977 | Waugh |
| 4,034,746 A | 7/1977 | Williams |
| 4,038,897 A | 8/1977 | Murray et al. |
| 4,038,987 A | 8/1977 | Komiya |
| 4,232,404 A | 11/1980 | Samuelson et al. |
| 4,309,777 A | 1/1982 | Patil |
| 4,349,921 A | 9/1982 | Kuntz |
| 4,467,802 A | 8/1984 | Maslanka |
| 4,470,158 A | 9/1984 | Pappas et al. |
| 4,545,374 A | 10/1985 | Jacobson |
| 4,550,450 A | 11/1985 | Kinnett |
| 4,622,959 A | 11/1986 | Marcus |
| 4,653,487 A | 3/1987 | Maale |
| 4,681,589 A | 7/1987 | Tronzo |
| 4,697,586 A | 10/1987 | Gazale |
| 4,714,469 A | 12/1987 | Kenna |
| 4,736,738 A | 4/1988 | Lipovsek et al. |
| 4,743,262 A | 5/1988 | Tronzo |
| 4,759,766 A | 7/1988 | Buettner-Janz et al. |
| 4,759,769 A | 7/1988 | Hedman et al. |
| 4,770,661 A | 9/1988 | Oh |
| H571 H | 2/1989 | Hollinger |
| 4,805,607 A | 2/1989 | Englehardt et al. |
| 4,819,334 A | 4/1989 | Mongeon |
| 4,863,476 A | 9/1989 | Shepperd |
| 4,874,389 A | 10/1989 | Downey |
| 4,875,474 A | 10/1989 | Border |
| 4,892,545 A | 1/1990 | Day et al. |
| 4,932,975 A | 6/1990 | Main et al. |
| 4,936,853 A | 6/1990 | Fabian et al. |
| 4,936,863 A | 6/1990 | Hofmann |
| 4,946,378 A | 8/1990 | Hirayama et al. |
| 4,986,826 A | 1/1991 | Roger |
| 4,997,432 A | 3/1991 | Keller |
| 5,004,476 A | 4/1991 | Cook |
| 5,022,576 A | 6/1991 | Jenq |
| 5,035,698 A | 7/1991 | Comparetto |
| 5,035,716 A | 7/1991 | Downey |
| 5,037,438 A | 8/1991 | Davidson |
| 5,062,850 A | 11/1991 | MacMillan et al. |
| 5,071,437 A | 12/1991 | Steffee |
| 5,108,442 A | 4/1992 | Smith |
| 5,122,130 A | 6/1992 | Keller |
| 5,122,142 A | 6/1992 | Pascaloff |
| 5,171,280 A | 12/1992 | Baumgartner |
| 5,192,327 A | 3/1993 | Brantigan |
| 5,211,645 A | 5/1993 | Baumgartner et al. |
| 5,228,455 A | 7/1993 | Barcel |
| 5,236,460 A | 8/1993 | Barber |
| 5,258,031 A | 11/1993 | Salib et al. |
| 5,271,737 A | 12/1993 | Baldwin et al. |
| 5,282,868 A | 2/1994 | Bahler |
| 5,290,312 A | 3/1994 | Kojimoto et al. |
| 5,306,308 A | 4/1994 | Gross et al. |
| 5,306,309 A | 4/1994 | Wagner et al. |
| 5,314,477 A | 5/1994 | Marnay |
| 5,326,366 A | 7/1994 | Pascarella et al. |
| 5,336,232 A | 8/1994 | Green et al. |
| 5,344,458 A | 9/1994 | Bonutti |
| 5,364,397 A | 11/1994 | Hayes et al. |
| 5,370,697 A | 12/1994 | Baumgartner |
| 5,383,888 A | 1/1995 | Zvenyatsky et al. |
| 5,395,317 A | 3/1995 | Kambin |
| 5,401,269 A | 3/1995 | Buttner-Janz et al. |

(56) References Cited

U.S. PATENT DOCUMENTS

| | | |
|---|---|---|
| 5,403,318 A | 4/1995 | Boehringer |
| 5,409,492 A | 4/1995 | Jones et al. |
| 5,423,825 A | 6/1995 | Levine |
| 5,425,773 A | 6/1995 | Boyd et al. |
| 5,431,658 A | 7/1995 | Moskovich |
| 5,443,514 A | 8/1995 | Steffee |
| 5,458,641 A | 10/1995 | Ramirez Jimeniz |
| 5,484,437 A | 1/1996 | Michelson |
| 5,489,307 A | 2/1996 | Kuslich et al. |
| 5,501,654 A | 3/1996 | Faille et al. |
| 5,505,732 A | 4/1996 | Michelson |
| 5,507,816 A | 4/1996 | Bullivant |
| 5,507,821 A | 4/1996 | Sennwald et al. |
| 5,509,934 A | 4/1996 | Cohen |
| 5,534,029 A | 7/1996 | Shima |
| 5,534,030 A | 7/1996 | Navarro et al. |
| 5,545,229 A | 8/1996 | Parsons et al. |
| 5,554,191 A | 9/1996 | Lahille et al. |
| 5,556,431 A | 9/1996 | Buttner-Janz |
| 5,562,736 A | 10/1996 | Ray et al. |
| 5,562,738 A | 10/1996 | Boyd et al. |
| 5,571,109 A | 11/1996 | Bertagnoli |
| 5,591,235 A | 1/1997 | Kuslich |
| 5,609,636 A | 3/1997 | Kohrs et al. |
| 5,658,347 A | 8/1997 | Sarkisian et al. |
| 5,674,296 A | 10/1997 | Bryan et al. |
| 5,676,701 A | 10/1997 | Yuan et al. |
| 5,683,465 A | 11/1997 | Shinn et al. |
| 5,702,469 A | 12/1997 | Whipple et al. |
| 5,702,486 A | 12/1997 | Craig et al. |
| 5,716,415 A | 2/1998 | Steffee |
| 5,720,751 A | 2/1998 | Jackson |
| 5,722,977 A | 3/1998 | Wihelmy |
| 5,755,798 A | 5/1998 | Papavero et al. |
| 5,755,811 A | 5/1998 | Tanamal et al. |
| 5,776,199 A | 7/1998 | Michelson |
| 5,782,830 A | 7/1998 | Farris |
| 5,782,832 A | 7/1998 | Larsen et al. |
| 5,797,909 A | 8/1998 | Michelson |
| 5,800,547 A | 9/1998 | Schafer et al. |
| 5,824,094 A | 10/1998 | Serhan et al. |
| D401,335 S | 11/1998 | Koros et al. |
| 5,865,848 A | 2/1999 | Baker |
| 5,885,300 A | 3/1999 | Tokuhashi et al. |
| 5,888,226 A | 3/1999 | Rogozinski |
| 5,895,428 A | 4/1999 | Berry |
| 5,897,593 A | 4/1999 | Kohrs et al. |
| 5,899,901 A | 5/1999 | Middleton |
| 5,899,941 A | 5/1999 | Nishijima et al. |
| 5,951,564 A | 9/1999 | Schroder et al. |
| 6,006,174 A | 12/1999 | Lin et al. |
| 6,010,502 A | 1/2000 | Bagby |
| 6,017,342 A | 1/2000 | Rinner |
| 6,022,353 A | 2/2000 | Fletcher |
| 6,033,405 A | 3/2000 | Winslow et al. |
| 6,036,692 A | 3/2000 | Burel et al. |
| 6,039,763 A | 3/2000 | Shelokov |
| 6,042,582 A | 3/2000 | Ray et al. |
| 6,059,790 A | 5/2000 | Sand et al. |
| 6,063,088 A | 5/2000 | Winslow |
| 6,063,121 A | 5/2000 | Xavier et al. |
| 6,080,155 A | 6/2000 | Michelson |
| 6,083,225 A | 7/2000 | Winslow et al. |
| 6,086,595 A | 7/2000 | Yonemura et al. |
| 6,096,038 A | 8/2000 | Michelson |
| 6,096,080 A | 8/2000 | Nicholson et al. |
| 6,102,950 A | 8/2000 | Vaccaro |
| 6,102,954 A | 8/2000 | Albrektsson et al. |
| 6,110,179 A | 8/2000 | Flivik et al. |
| 6,113,602 A | 9/2000 | Sand |
| 6,113,637 A | 9/2000 | Gill et al. |
| 6,113,638 A | 9/2000 | Williams et al. |
| 6,126,660 A | 10/2000 | Dietz |
| 6,126,674 A | 10/2000 | Janzen |
| 6,145,426 A | 11/2000 | Ward |
| 6,146,421 A | 11/2000 | Gordon et al. |
| 6,156,040 A | 12/2000 | Yonemura et al. |
| 6,159,215 A | 12/2000 | Urbahns et al. |
| 6,171,339 B1 | 1/2001 | Houfburg et al. |
| 6,174,311 B1 | 1/2001 | Branch et al. |
| 6,179,874 B1 | 1/2001 | Cauthen |
| 6,224,599 B1 | 5/2001 | Baynham et al. |
| 6,238,414 B1 | 5/2001 | Griffiths |
| 6,241,769 B1 | 6/2001 | Nicholson et al. |
| 6,251,140 B1 | 6/2001 | Marino et al. |
| 6,261,296 B1 | 7/2001 | Aebi et al. |
| 6,264,655 B1 | 7/2001 | Pisharodi |
| 6,270,498 B1 | 8/2001 | Michelson |
| 6,296,647 B1 | 10/2001 | Robioneck et al. |
| 6,309,421 B1 | 10/2001 | Pisharodi |
| 6,368,350 B1 | 4/2002 | Erickson et al. |
| 6,368,353 B1 | 4/2002 | Arcand |
| 6,375,681 B1 | 4/2002 | Truscott |
| 6,395,030 B1 | 5/2002 | Songer et al. |
| 6,402,785 B1 | 6/2002 | Zdeblick et al. |
| 6,413,278 B1 | 7/2002 | Marchosky |
| 6,436,139 B1 | 8/2002 | Shapiro et al. |
| 6,440,142 B1 | 8/2002 | Ralph et al. |
| 6,440,168 B1 | 8/2002 | Cauthen |
| 6,440,169 B1 | 8/2002 | Elberg et al. |
| 6,368,351 B1 | 9/2002 | Glenn et al. |
| 6,447,547 B1 | 9/2002 | Michelson |
| 6,478,800 B1 | 11/2002 | Fraser et al. |
| 6,478,801 B1 | 11/2002 | Ralph et al. |
| 6,478,823 B1 | 11/2002 | Michelson |
| 6,500,206 B1 | 12/2002 | Bryan |
| 6,517,544 B1 | 2/2003 | Michelson |
| 6,558,424 B2 | 5/2003 | Thalgott |
| 6,565,574 B2 | 5/2003 | Michelson |
| 6,595,995 B2 | 7/2003 | Zdelblick et al. |
| 6,599,294 B2 | 7/2003 | Fuss et al. |
| 6,610,065 B1 | 8/2003 | Branch et al. |
| 6,613,091 B1 | 9/2003 | Zdelblick et al. |
| 6,626,943 B2 | 9/2003 | Eberlein et al. |
| 6,635,060 B2 | 10/2003 | Hanson et al. |
| 6,641,582 B1 | 11/2003 | Hanson et al. |
| 6,641,614 B1 | 11/2003 | Wagner et al. |
| 6,652,533 B2 | 11/2003 | O'Neil |
| 6,652,534 B2 | 11/2003 | Zucherman et al. |
| 6,679,886 B2 | 1/2004 | Weikel et al. |
| 6,712,819 B2 | 3/2004 | Zucherman et al. |
| 6,712,825 B2 | 3/2004 | Aebi et al. |
| 6,733,505 B2 | 5/2004 | Li |
| 6,740,118 B2 | 5/2004 | Eisermann et al. |
| 6,746,454 B2 | 6/2004 | Winterbottom et al. |
| 6,755,841 B2 | 6/2004 | Fraser et al. |
| 6,770,074 B2 | 8/2004 | Michelson |
| 6,824,565 B2 | 11/2004 | Muhanna et al. |
| 6,835,207 B2 | 12/2004 | Zacouto et al. |
| 6,875,213 B2 | 4/2005 | Michelson |
| 6,896,676 B2 | 5/2005 | Zubok et al. |
| 6,936,071 B1 | 8/2005 | Marnay et al. |
| 6,964,687 B1 | 11/2005 | Bernerd et al. |
| 6,966,912 B2 | 11/2005 | Michelson |
| 7,037,340 B2 | 5/2006 | Gau |
| 7,048,766 B2 | 5/2006 | Ferree |
| 7,081,120 B2 | 7/2006 | Li et al. |
| 7,083,649 B2 | 8/2006 | Zucherman et al. |
| 7,087,057 B2 | 8/2006 | Konieczynski et al. |
| 7,118,580 B1 | 10/2006 | Beyersdorlf et al. |
| 7,153,303 B2 | 12/2006 | Squires et al. |
| 7,169,182 B2 | 1/2007 | Errico et al. |
| 7,204,852 B2 | 4/2007 | Marnay et al. |
| 7,238,203 B2 | 7/2007 | Bagga et al. |
| 7,252,673 B2 | 8/2007 | Lim |
| 7,300,441 B2 | 11/2007 | Haid |
| 7,306,607 B2 | 12/2007 | Metzger |
| 7,491,204 B2 | 2/2009 | Marnay |
| 7,547,309 B2 | 6/2009 | Bertagnoli et al. |
| 7,575,576 B2 | 8/2009 | Zubok et al. |
| 7,641,692 B2 | 1/2010 | Bryan et al. |
| 7,648,520 B2 | 1/2010 | Markworth |
| 7,708,776 B1* | 5/2010 | Blain .................. A61F 2/4425 606/279 |

(56) References Cited

U.S. PATENT DOCUMENTS

| | | |
|---|---|---|
| 7,763,024 B2 | 7/2010 | Bertagnoli et al. |
| 7,803,162 B2 | 9/2010 | Marnay et al. |
| 7,811,325 B2 | 10/2010 | Cannon et al. |
| 7,837,732 B2 | 11/2010 | Zucherman et al. |
| 8,025,684 B2 | 9/2011 | Garcia-Bengochea et al. |
| 8,083,746 B2 | 12/2011 | Novak |
| 8,414,595 B2 | 4/2013 | Baker |
| 8,518,045 B2 | 8/2013 | Szanto |
| 8,998,990 B2 * | 4/2015 | Bertagnoli ............. A61B 17/15 623/17.16 |
| 2002/0016633 A1 | 2/2002 | Lin et al. |
| 2002/0049497 A1 | 4/2002 | Mason |
| 2002/0065558 A1 | 5/2002 | Varga et al. |
| 2002/0072752 A1 | 6/2002 | Zucherman et al. |
| 2002/0077702 A1 | 6/2002 | Castro |
| 2002/0165612 A1 | 11/2002 | Gerber et al. |
| 2003/0028197 A1 | 2/2003 | Hanson et al. |
| 2003/0083747 A1 | 5/2003 | Winterbottom et al. |
| 2003/0135275 A1 | 7/2003 | Garcia et al. |
| 2003/0191534 A1 | 10/2003 | Viart et al. |
| 2003/0195631 A1 | 10/2003 | Ferree |
| 2003/0208273 A1 | 11/2003 | Eisermann et al. |
| 2003/0233145 A1 | 12/2003 | Landry et al. |
| 2004/0002758 A1 | 1/2004 | Landry et al. |
| 2004/0002761 A1 | 1/2004 | Rogers et al. |
| 2004/0010316 A1 | 1/2004 | Williams et al. |
| 2004/0024462 A1 | 2/2004 | Ferree et al. |
| 2004/0030387 A1 | 2/2004 | Landry et al. |
| 2004/0073312 A1 | 4/2004 | Eisermann et al. |
| 2004/0097929 A1 | 5/2004 | Branch |
| 2004/0117022 A1 | 6/2004 | Marnay et al. |
| 2004/0133278 A1 | 7/2004 | Marino et al. |
| 2004/0138749 A1 | 7/2004 | Zucherman et al. |
| 2004/0138750 A1 | 7/2004 | Mitchell |
| 2004/0143332 A1 | 7/2004 | Krueger et al. |
| 2004/0172133 A1 | 9/2004 | Gerber et al. |
| 2004/0215198 A1 | 10/2004 | Marnay et al. |
| 2004/0225295 A1 | 11/2004 | Zubok et al. |
| 2004/0225364 A1 * | 11/2004 | Richelsoph ............ A61F 2/4425 623/17.13 |
| 2004/0225365 A1 | 11/2004 | Eisermann et al. |
| 2004/0225366 A1 | 11/2004 | Eisermann et al. |
| 2005/0021042 A1 | 1/2005 | Marnay et al. |
| 2005/0021145 A1 | 1/2005 | de Villiers et al. |
| 2005/0021146 A1 | 1/2005 | de Villiers et al. |
| 2005/0043802 A1 | 2/2005 | Eisermann et al. |
| 2005/0060034 A1 | 3/2005 | Berry et al. |
| 2005/0060035 A1 | 3/2005 | Errico et al. |
| 2005/0085917 A1 | 4/2005 | Marnay et al. |
| 2005/0113926 A1 | 5/2005 | Zucherman et al. |
| 2005/0125061 A1 | 6/2005 | Zucherman et al. |
| 2005/0143747 A1 | 6/2005 | Zubok et al. |
| 2005/0143749 A1 | 6/2005 | Zalenski et al. |
| 2005/0143820 A1 | 6/2005 | Zucherman et al. |
| 2005/0154462 A1 | 7/2005 | Zucherman et al. |
| 2005/0159818 A1 | 7/2005 | Blain |
| 2005/0165408 A1 | 7/2005 | Puno et al. |
| 2005/0203626 A1 | 9/2005 | Sears et al. |
| 2005/0228500 A1 | 10/2005 | Kim et al. |
| 2005/0234465 A1 | 10/2005 | McCombs |
| 2005/0246022 A1 | 11/2005 | Zubok et al. |
| 2005/0251260 A1 | 11/2005 | Gerber et al. |
| 2005/0261769 A1 | 11/2005 | Moskowitz et al. |
| 2005/0267581 A1 | 12/2005 | Marnay et al. |
| 2006/0009796 A1 | 1/2006 | Carusillo |
| 2006/0030856 A1 | 2/2006 | Drewry et al. |
| 2006/0030860 A1 | 2/2006 | Peterman |
| 2006/0036326 A1 | 2/2006 | Baumgartner et al. |
| 2006/0041313 A1 | 2/2006 | Allard et al. |
| 2006/0064100 A1 | 3/2006 | Bertagnoli et al. |
| 2006/0089656 A1 | 4/2006 | Allard et al. |
| 2006/0100633 A1 | 5/2006 | Michelson |
| 2006/0116769 A1 | 6/2006 | Marnay et al. |
| 2006/0149273 A1 | 7/2006 | Ross et al. |
| 2006/0149378 A1 | 7/2006 | Chase et al. |
| 2006/0210594 A1 | 9/2006 | Trieu |
| 2006/0217729 A1 | 9/2006 | Eskridge |
| 2006/0217809 A1 | 9/2006 | Albert et al. |
| 2006/0235533 A1 | 10/2006 | Blain |
| 2006/0241641 A1 | 10/2006 | Albans et al. |
| 2006/0259147 A1 | 11/2006 | Krishna et al. |
| 2006/0265077 A1 | 11/2006 | Zwirkoski |
| 2007/0055378 A1 * | 3/2007 | Ankney ............. A61B 17/1671 623/17.15 |
| 2007/0162130 A1 * | 7/2007 | Rashbaum ............ A61F 2/4425 623/17.11 |
| 2007/0162134 A1 | 7/2007 | Marnay et al. |
| 2007/0179615 A1 | 8/2007 | Heinz et al. |
| 2007/0191955 A1 | 8/2007 | Zucherman et al. |
| 2007/0198089 A1 | 8/2007 | Moskowitz et al. |
| 2007/0198093 A1 | 8/2007 | Brodke et al. |
| 2007/0213821 A1 | 9/2007 | Kwak et al. |
| 2007/0225812 A1 | 9/2007 | Gill |
| 2007/0265707 A1 | 11/2007 | Marnay et al. |
| 2008/0133013 A1 | 6/2008 | Duggal et al. |
| 2008/0140204 A1 | 6/2008 | Heinz |
| 2008/0140208 A1 | 6/2008 | Zucherman et al. |
| 2008/0161923 A1 | 7/2008 | Parsons |
| 2008/0215156 A1 | 9/2008 | Duggal et al. |
| 2008/0228275 A1 | 9/2008 | Cannon et al. |
| 2008/0243125 A1 | 10/2008 | Guzman |
| 2009/0043392 A1 | 2/2009 | Duggal et al. |
| 2009/0043393 A1 | 2/2009 | Duggal et al. |
| 2009/0069894 A1 | 3/2009 | Duggal et al. |
| 2009/0076608 A1 | 3/2009 | Gordon et al. |
| 2009/0149964 A1 | 6/2009 | May |
| 2009/0255390 A1 | 10/2009 | Chaffin |
| 2009/0326540 A1 | 12/2009 | Estes |
| 2010/0070042 A1 | 3/2010 | Bryan et al. |
| 2010/0217395 A1 | 8/2010 | Bertagnoli et al. |
| 2010/0228351 A1 | 9/2010 | Ankney et al. |
| 2010/0234954 A1 | 9/2010 | Justis et al. |
| 2010/0280617 A1 | 11/2010 | Coppes et al. |
| 2010/0292800 A1 | 11/2010 | Zubok |
| 2010/0298941 A1 | 11/2010 | Hes et al. |
| 2010/0324690 A1 | 12/2010 | Cannon et al. |
| 2011/0082556 A1 | 4/2011 | Duggal et al. |
| 2011/0087331 A1 | 4/2011 | Reichen et al. |
| 2011/0106263 A1 | 5/2011 | Eisermann et al. |
| 2011/0118845 A1 | 5/2011 | Overes et al. |
| 2011/0172773 A1 | 7/2011 | Reichen et al. |
| 2011/0230887 A1 | 9/2011 | Bickenbach |
| 2011/0282458 A1 | 11/2011 | Aferzon et al. |
| 2011/0295374 A1 | 12/2011 | Bryan et al. |
| 2011/0320001 A1 | 12/2011 | Hughes et al. |
| 2011/0320003 A1 | 12/2011 | Duggal et al. |
| 2012/0083888 A1 | 4/2012 | Moumene et al. |
| 2012/0101579 A1 | 4/2012 | de Villiers et al. |
| 2012/0101582 A1 | 4/2012 | Raiszadeh et al. |
| 2012/0109316 A1 | 5/2012 | Marnay et al. |
| 2012/0232663 A1 | 9/2012 | Zipnick |
| 2012/0290093 A1 | 11/2012 | Hansell et al. |
| 2012/0310349 A1 | 12/2012 | Gordon et al. |
| 2012/0316648 A1 | 12/2012 | Lambrecht et al. |
| 2013/0023990 A1 | 1/2013 | Zipnick et al. |
| 2013/0110240 A1 | 5/2013 | Hansell et al. |
| 2013/0138217 A1 | 5/2013 | Laurence et al. |
| 2013/0204255 A1 | 8/2013 | Milburn |
| 2014/0046331 A1 | 2/2014 | Amos |
| 2014/0325855 A1 | 11/2014 | Bozic |

FOREIGN PATENT DOCUMENTS

| | | |
|---|---|---|
| CN | 101631517 | 1/2010 |
| DE | 2263842 | 7/1974 |
| DE | 2804936 | 8/1979 |
| DE | 3023353 | 4/1981 |
| DE | 3526742 | 1/1987 |
| DE | 4328690 | 3/1995 |
| EP | 0077159 | 4/1983 |
| EP | 0333990 | 7/1993 |
| EP | 0770367 | 5/1997 |
| EP | 0712607 | 2/2002 |
| EP | 1793749 | 6/2007 |

(56) References Cited

FOREIGN PATENT DOCUMENTS

| | | |
|---|---|---|
| EP | 2120799 | 11/2009 |
| FR | 2718635 | 10/1995 |
| FR | 2724108 | 3/1996 |
| FR | 2737656 | 2/1997 |
| FR | 2742653 | 6/1997 |
| FR | 2795945 | 1/2001 |
| JP | 2261446 | 10/1990 |
| JP | 2010-521244 | 6/2010 |
| WO | WO 1991/013598 | 9/1991 |
| WO | WO 1998/034552 | 8/1998 |
| WO | WO 2001/001893 | 1/2001 |
| WO | WO 2001/019295 | 3/2001 |
| WO | WO 2002/071986 | 9/2002 |
| WO | WO 2003/053290 | 7/2003 |
| WO | WO 2004/019828 | 3/2004 |
| WO | WO 2004/098380 | 11/2004 |
| WO | WO 2005/051243 | 6/2005 |
| WO | WO 2005/053580 | 6/2005 |
| WO | WO 2006/012608 A1 | 2/2006 |
| WO | WO 2006/033067 | 3/2006 |
| WO | WO 2006/036580 | 4/2006 |
| WO | WO 2008/014258 | 1/2008 |
| WO | WO 2008/112956 | 9/2008 |
| ZA | 2009/05900 | 5/2010 |

OTHER PUBLICATIONS

Japanese Patent Application No. 2009-553793: Notification of Reasons for Rejection dated Dec. 3, 2012, 2 pages.
International Patent Application No. PCT/US2005/33007: International Search Report dated Oct. 20, 2006, 1 page.
International Patent Application No. PCT/US2008/056960: International Search Report dated Jul. 28, 2008, 6 pages.
"A New Tibia Plateau", The Journal of Bone and Joint Surgery, Jul. 1, 1970, 52-A (5), 2 pages.
"Here's a Good Skate", The Journal of Bone and Joint Surgery, Sep. 1, 1971, 53-A(6), 2 pages.
"Amended Judgment Awarding Enhanced Damages, Prejudgment Interest and Attorney Fees" (Filed Nov. 9, 2009, Doc. 521), 2 pages.
"Amended Order Denying Defendants' Motion for Summary Judgment of Invalidity Under 35 U.S.C. § 103" (Dated Nov. 6, 2008, Doc. 332), 20 pages.
"Amended Order Denying Medtronic's Renewed Motion for Judgment as a Matter of Law and Alternative Motion for a New Trial" (Filed Aug. 20, 2009, doc. 494), 30 pages.
"Appeal from the US District Court: *Spine Solutions, Inc.* vs. *Medtronic Sofamor Danek USA, Inc.*", In the United States Court for the Western District of Tennessee, Case No. 07-CV-02175, Decided: Sep. 9, 2010, 28 pages.
"Brief in Support of Medtronic's Motion for Judgment as a Matter of Law on the Obviousness of the '071 Patent, No Willful Infringement and No Lost Profits" (Dec. 4, 2008, Doc. 406), *Spine Solutions, Inc, v. Medtronic Sofamor Danek, Inc. et al.*, U.S. District Court, Western District of Tennessee, Civil Docket # 2:07-cv-02175-JPM-dkv, 9 pages.
"Citation of Supplemental Authority in Support of Medtronic's Renewed Motion for Judgment as a Matter of Law and Alternative Motion for a New Trial," with accompanying exhibit (Feb. 18, 2009, Docs. 453, 453-2), *Spine Solutions, Inc, v. Medtronic Sofamor Danek, Inc. et al.*, U.S. District Court, Western District of Tennessee, Civil Docket # 2:07-cv-02175-JPM-dkv, 17 pages.
"Judgment Awarding Enhanced Damages, Post-Dec. 31, 2007 Damages, Pre- and Post-Judgment Interest, and Injunctive Relief" (Filed Aug. 26, 2009, Doc. 497), 2 pages.
"Judgment" (Dec. 8, 2008, Doc. 412), *Spine Solutions, Inc, v. Medtronic Sofamor Danek, Inc. et al.*, U.S. District Court, Western District of Tennessee, Civil Docket # 2:07-cv-02175-JPM-dkv, 2 pages.
"Jury Verdict Form" (Dec. 5, 2008, Doc. 411), *Spine Solutions, Inc, v. Medtronic Sofamor Danek, Inc. et al.*, U.S. District Court, Western District of Tennessee, Civil Docket # 2:07-cv-02175-JPM-dkv, 4 pages.

"Memorandum in Support of Medtronic's Renewed for Judgment as a Matter of Law and Alternative Motion for a New Trial," with accompanying exhibits (Dec. 22, 2008, Docs. 420-2 through 420-22), *Spine Solutions, Inc, v. Medtronic Sofamor Danek, Inc. et al.*, U.S. District Court, Western District of Tennessee, Civil Docket # 2:07-cv-02175-JPM-dkv, 614 pages.
"Memorandum in Support of Plaintiffs' Motion for Judgment as a Matter of Law that the '071 Patent Is Not Invalid for Obviousness" (Dec. 4, 2008, Doc. 407-2), *Spine Solutions, Inc, v. Medtronic Sofamor Danek, Inc. et al.*, U.S. District Court, Western District of Tennessee, Civil Docket # 2:07-cv-02175-JPM-dkv, 6 pages.
"Order Amending and Altering the Judgment Entered on Aug. 26, 2009 to Alter the Amount of Damages and Interest Awarded and to Amend the Judgment to Provide for an Award of Attorney Fees" (Filed Nov. 9, 2009, Doc. 520), 20 pages.
"Order Denying Defendants' Motion for Summary Judgment of Invalidity under 35 U.S.C. § 103" (Dated Sep. 30, 2008, Doc. 317), 20 pages.
"Order Denying Defendants' Motion for Summary Judgment of No Willful Infringement" (Dated Sep. 30, 2008, Doc. 318), 12 pages.
"Order Denying Defendants' Motion for Summary Judgment of Non-infringement on 0-MAV; Order Granting Plaintiff Spine Solutions, Inc.'s Motion for Partial Summary Judgment of Infringement of Claims 1 and 2 of U.S. Pat. No. 6,939,071" (Dated Sep. 30, 2008, Doc. 313), 14 pages.
"Order Denying Defendants' Motion for Summary Judgment of Non-infringement, or in the Alternative for Invalidity; Order Granting Plaintiff Spine Solutions, Inc.'s Motion for Partial Summary Judgment Dismissing Medtronic's 35 U.S.C. § 112 Defenses" (Dated Sep. 30, 2008, Doc. 314), 16 pages.
"Order Denying Plaintiff Spine Solutions, Inc.'s Motion for Summary Judgment Regarding the Obviousness Defense" (Filed Nov. 6, 2008, Doc. 333) 2 pages.
"Order Denying Plaintiffs' Motion to Unseal the Court's Summary Judgment Orders, Post-Trial Orders, and Judgments" (Filed Dec. 23, 2009, doc. 525), 8 pages.
"Order Granting in Part and Denying in Part Plaintiffs' Motion for Treble Damages, Award of Attorney Fees, Expert Witness Fees, Expenses, Post Dec. 31, 2007 damages, and Pre- and Post-Judgment Interest" (Filed Aug. 26, 2009, Doc. 495), 24 pages.
"Order Granting Plaintiff Spine Solutions, Inc.'s Motion for Partial Summary Judgment (1) that the Asserted Claims of the '071 Patent Are Not Anticipated; and (2) that the (a) '785 Patent [No. 6,402,785], (b) Dr. Zdeblick and Mr. McKay's Alleged Invention, and (c) Numerous Unexplained References Are Not Prior Art" (Dated Sep. 30, 2008, Doc. 315), 14 pages.
"Order Granting Plaintiff Spine Solutions, Inc.'s Motion for Partial Summary Judgment of Failure of Defendants to State a Legal Defense or Claim for Relief Based on Inequitable Conduct" (Dated Sep. 30, 2008, Doc. 316), 10 pages.
"Order Granting Plaintiffs' Motion for Permanent Injunction" (Filed Aug. 26, 2009, doc. 496), 24 pages.
"Plaintiffs' Memorandum in Opposition to Medtronic's Renewed Motion for Judgment as a Matter of Law and Alternative Motion for a New Trial" (Jan. 23, 2009, Doc. 439), *Spine Solutions, Inc, v. Medtronic Sofamor Danek, Inc. et al.*, U.S. District Court, Western District of Tennessee, Civil Docket # 2:07-cv-02175-JPM-dkv, 41 pages.
"Plaintiffs' Memorandum in Response to Medtronic's Reply Memorandum and Citation of Supplemental Authority, Regarding Medtronic's Renewed Motion for Judgment as a Matter of Law and Alternative Motion for a New Trial" (Mar. 11, 2009, Doc. 463), *Spine Solutions, Inc, v. Medtronic Sofamor Danek, Inc. et al.*, U.S. District Court, Western District of Tennessee, Civil Docket # 2:07-cv-02175-JPM-dkv, 26 pages.
"Plaintiffs' Motion and Supporting Memorandum to Unseal the Court's Post-Trial Orders, Judgments, and Summary Judgment Orders" (Filed Nov. 17, 2009, doc. 523), 7 pages.
"Reply Memorandum in Support of Medtronic's Renewed Motion for Judgment as a Matter of Law and Alternative Motion for a New Trial", with accompanying exhibit (Feb. 10, 2009, Docs. 449, 449-2), *Spine Solutions, Inc, v. Medtronic Sofamor Danek, Inc. et*

(56) References Cited

OTHER PUBLICATIONS al., U.S. District Court, Western District of Tennessee, Civil Docket # 2:07-cv-02175-JPM-dkv, 71 pages.

Ahrens et al., "Normal Joint Mobility is Maintained With an Artificial Disc Prosthesis", Waldemar Link GmbH & Co., 1999, 4 pages.

David S. Hungerford, M.D. and Robert V. Kenna, "Preliminary Experience with a Total Knee Prosthesis with Porous Coating Used without Cement", Clinical Orthopaedics and Related Research, Cementless Total Knee Prosthesis, No. 176, Jun. 1983, 95-107.

Ducheyne, "Declaration of Paul Ducheyne Under 37 C.F.R. § 1.132", Feb. 19, 2010, 22 pages.

European Patent Application No. EP 05795413: Supplementary European Search Report, dated Aug. 10, 2011, 7 pages.

Hoogland et al., "Total Lumbar Intervertebral Disc Replacement: Testing of a New Articulating Spacer in Human Cadaver Spines", 24th Annual ORS, Dallas, Texas, Feb. 21-23, 1978, 102.

In the United States Patent and Trademark Office, "Notice of Intent to Issue Ex Parte Reexamination Certificate", Ex Parte Reexamination No. 90/010,655 and No. 90/009,542, Filed Aug. 24, 2009 and Jul. 24, 2009, date mailed Jul. 14, 2010, 9 pages.

In the United States Patent and Trademark Office, "Patent Owner's Response Pursuant to 37 C.F.R. § 1.550 in Merged Ex Parte Reexamination of U.S. Pat. No. 6,936,071," Ex Parte Reexamination No. 90/010,655 and No. 90/009,542, Filed Aug. 24, 2009 and Jul. 24, 2009, dated May 19, 2010, 36 pages.

In the United States Patent and Trademark Office, "Request for Ex Parte Reexamination", in re patent of: Marnay et al., U.S. Pat. No. 6,936,071, filed on Jul. 24, 2009, 70 pages.

In the United States Patent and Trademark Office, "Request for Ex Parte Reexamination", in re patent of: Marnay et al., U.S. Pat. No. 6,936,071, filed on Aug. 24, 2009, 23 pages.

In the United States Patent and Trademark Office, in Re. U.S. Appl. No. 10/070,823, filed Jul. 15, 2002 Notice of Allowance dated Jul. 13, 2006, 4 pages.

In the United States Patent and Trademark Office, in Re. U.S. Appl. No. 10/070,823, filed Jul. 15, 2002, Final Rejection dated Aug. 23, 2005, 11 pages.

In the United States Patent and Trademark Office, in Re. U.S. Appl. No. 10/070,823, filed Jul. 15, 2002, Non-Final Office Action, dated Sep. 23, 2004, 10 pages.

In the United States Patent and Trademark Office, in Re. U.S. Appl. No. 10/318,078, filed Dec. 13, 2002, Issue Notice dated Mar. 28, 2007, 1 page.

In the United States Patent and Trademark Office, in Re. U.S. Appl. No. 10/318,078, filed Dec. 13, 2002, Final Rejection dated Aug. 1, 2006, 7 pages.

In the United States Patent and Trademark Office, in Re. U.S. Appl. No. 10/318,078, filed Dec. 13, 2002, Final Rejection dated Nov. 12, 2004, 7 pages.

In the United States Patent and Trademark Office, in Re. U.S. Appl. No. 10/318,078, filed Dec. 13, 2002, Non-Final Office Action dated Apr. 21, 2004, 6 pages.

In the United States Patent and Trademark Office, in Re. U.S. Appl. No. 10/318,078, filed Dec. 13, 2002, Non-Final Office Action dated Aug. 8, 2005, 5 pages.

In the United States Patent and Trademark Office, in Re. U.S. Appl. No. 10/318,078, filed Dec. 13, 2002, Notice of Allowance dated Feb. 26, 2007, 7 pages.

In the United States Patent and Trademark Office, in Re. U.S. Appl. No. 10/070,823, filed Jul. 15, 2002 Advisory Action dated Jun. 22, 2006, 2 pages.

In the United States Patent and Trademark office, in Re. U.S. Appl. No. 10/998,951, filed Nov. 30, 2004, Non-Final Office Action, dated Aug. 19, 2009, 11 pages.

In the United States Patent and Trademark office, in Re. U.S. Appl. No. 10/998,951, filed Nov. 30, 2004, Response to Non-Final Office Action, dated Feb. 19, 2010, 37 pages.

In the United States Patent and Trademark Office, in Re. U.S. Appl. No. 10/622,535, filed Jul. 21, 2003: Non Final Office Action dated Apr. 26, 2007, 6 pages.

In the United States Patent and Trademark Office, in Re. U.S. Appl. No. 10/622,535, filed Jul. 21, 2003: Non Final Office Action dated Aug. 30, 2005, 7 pages.

In the United States Patent and Trademark Office, in Re. U.S. Appl. No. 10/622,535, filed Jul. 21, 2003: Final Office Action dated Feb. 6, 2009, 7 pages.

In the United States Patent and Trademark Office, in Re. U.S. Appl. No. 10/622,535, filed Jul. 21, 2003: Non Final Office Action dated Jan. 31, 2008, 7 pages.

In the United States Patent and Trademark Office, in Re. U.S. Appl. No. 10/622,535, filed Jul. 21, 2003: Non Final Office Action dated Nov. 8, 2006, 6 pages.

In the United States Patent and Trademark Office, in Re. U.S. Appl. No. 10/622,535, filed Jul. 21, 2003: Non Final Office Action dated Sep. 12, 2007, 6 pages.

In the United States Patent and Trademark Office, in Re. U.S. Appl. No. 10/622,535, filed Jul. 21, 2003: Notice of Allowance dated Jul. 20, 2009, 3 pages.

In the United States Patent and Trademark Office, in Re. U.S. Appl. No. 10/622,535, filed Jul. 21, 2003: Final Rejection dated May 23, 2006, 6 pages.

In the United States Patent and Trademark Office, in Re. U.S. Appl. No. 10/622,535, filed Jul. 21, 2003: Notice of Allowance dated Nov. 17, 2009, 4 pages.

In the United States Patent and Trademark Office, in Re. U.S. Appl. No. 11/512,327, filed Aug. 30, 2006: Notice of Allowance dated Oct. 8, 2009, 4 pages.

In the United States Patent and Trademark Office, in Re. U.S. Appl. No. 11/512,327, filed Aug. 30, 2006, Final Rejection dated Jun. 23, 2009, 6 pages.

In the United States Patent and Trademark Office, in Re. U.S. Appl. No. 11/512,327, filed Aug. 30, 2006, Non Final Rejection dated Oct. 6, 2008, 6 pages.

Marnay, "L'Arthroplastie Intervertebrale Lombaire", La Revue de Medicine Orthopedique, Jun.-Sep. 1991, No. 25, 48-55.

Marnay, "Lumbar Intervertebral Arthroplasty", English Translation of, "L'Arthroplastie Intervertebrale Lombaire", La Revue de Medicine Orthopedique, Jun.-Sep. 1991, No. 25, 48-55.

Marnay, "Declaration of Thierry Marnay Under 37 C.F.R. § 1.132", Feb. 19, 2010, 24 pages.

Nichols, "Declaration of David Nichols Under 37 C.F.R. § 1.132", Feb. 19, 2010, 7 pages.

PACER Docket sheet from *Spine Solutions, Inc. v. Medtronic Sofamor Danek, Inc. et al.*, U.S, District Court, Western District of Tennessee, Civil Docket # 2:07-cv-02175-JPM-dkv, As of May 19, 2009, 36 pages.

Robert E. Tooms, "Arthroplasty of ankle and knee", Campbell's Operative Orthopaedics, Seventh Edition, vol. Two, ed. A.H. Crenshaw, (St. Louis, Washington, D.C., Toronto: The C.V. Mosby Company 1987), 1145-1152.

Robert V. Kenna and David S. Hungerford, M.D., "Design Rational for the Porous Coated Anatomic Total Knee System," Total Knee Arthroplasty, A Comprehensive Approach, ed. David S. Hungerford, M.D., Kenneth A. Krackow, M.D., and Robert V. Kenna (Baltimore/London: Williams & Wilkins 1984), 71-88.

*Spine Solutions, Inc, v, Medtronic Sofamor Danek, Inc. and Medtronic Sofamor Danek USA, Inc.*, U.S. District Court, Western District of Tennessee, Civil Action No. 2:07-cv-02175-JPM, Answer and Counterclaims, May 4, 2007, 6 pages.

*Spine Solutions, Inc, v, Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions, Inc.'s Opening Markman Brief, Feb. 19, 2008, 27 pages.

*Spine Solutions, Inc. v. Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions, Inc.'s Response to Defendants' Motion to Amend Their Answer to Allege Inequitable Conduct, Dec. 7, 2007, 25 pages.

*Spine Solutions, Inc. v. Medtronic Sofamor Danek, Inc. and Medtronic Sofamor Danek USA, Inc.*, US. District Court, Western District of

(56) References Cited

OTHER PUBLICATIONS

Tennessee, Civil Action No. 2:07-cv-02175-JPM, Defendants' Opening Markman Brief, Feb. 19, 2008, 29 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Expert Report #2, Rebuttal to other reports in this litigation, Paul Ducheyne, Ph.D, Dec. 21, 2007, 36 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Expert Report of Charles A. Laff, Nov. 21, 2007, 12 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Rebuttal Expert Report of Mark. E. Nusbaum, Nov. 21, 2007, 42 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Expert Report of Dr. Thomas A. Zdeblick, M.D., Nov. 21, 2007, 77 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Defendants' Responsive Markman Brief, Mar. 17, 2008, 26 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions' Responsive Markman Brief, Mar. 17, 2008, 26 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Defendants' Reply Markman Brief, Mar. 31, 2008, 21 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions, Inc.'s Reply Markman Brief, Mar. 31, 2008, 39 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions, Inc.'s Reply Memorandum in Support of Motion for Partial Summary Judgment of Failure of Defendants to State a Legal Defense or Claim for Relief Based on Inequitable Conduct, Mar. 31, 2008, 62 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Reply Brief in Support of Plaintiff Spine Solutions, Inc.'s Motion for Partial Summary Judgment Dismissing Medtronic's 35 U.S.C. 5 112 Defenses, Mar. 31, 2008, 25 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions, Inc.'s Motion for Leave to File a Surreply to Defendants' Reply Markman Brief, Apr. 7, 2008 7 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Plaintiff Spine Solutions, Inc.'s Motion for Leave to File a Response to DefendantsJ Surreply Memorandum Regarding Plaintiffs Motion for Partial Summary Judgment of Failure of Defendants to State a Legal Defense or Claim for Relief Based on Inequitable Conduct and a Declaration of Marvin Petry in Support Thereto, Jun. 25, 2008, 2 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Defendants' Supplemental Brief in Support of Their Motion for Summary Judgment of Invalidity Under 35 U.S.C. § 103, Jun. 19, 2008, 31 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Order Following Markman Hearing, Jul. 2, 2008, 36 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Defendants' Medtronic Sofamor Danek, inc. and Medtronic Sofamor Danek USA, Inc.'s Sixth Supplemental Answers and Objections to Plaintiffs First Set of Interrogatories, Dec. 14, 2007, 40 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Plaintiffs Supplemental Response to Defendants' Interrogatory No. 2 (Relating to Conception, Reduction to Practice, First Sale), Oct. 29, 2007, 8 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Expert Report of Stephen D. Cook, Ph.D., Nov. 21, 2007, 202 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Defendants' Third Supp'l Answers & Objections to Plaintiffs First Set of Interrogatories Nos. 1-6, Oct. 15, 2007, 58 pages.
*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Amended Answer and Counterclaims, Nov. 21, 2007, 187 pages.
Szpalski et al., "Spine arthroplasty: a historical review," Eur. Spine J., Oct. 2002, 11(Suppl. 2), S65-S84.
Transcript Pages: pp. 1441-1639, 1644-1682 (Dec. 3-4, 2008), *Spine Solutions, Inc,* v. *Medtronic Sofamor Danek, Inc. et al.*, U.S. District Court, Western District of Tennessee, Civil Docket # 2:07-cv-02175-JPM-dkv, 246 pages.
Transcript Pages: pp. 1842-1892, 1899-1944 (Dec. 4-5, 2008), *Spine Solutions, Inc,* v. *Medtronic Sofamor Danek, Inc. et al.*, U.S. District Court, Western District of Tennessee, Civil Docket # 2:07-cv-02175-JPM-dkv, 103 pages.
Transcript Pages: pp. 345-535, 544-644, 669-700 (Nov. 25-26, 2008), *Spine Solutions, Inc,* v. *Medtronic Sofamor Danek, Inc. et al.*, U.S. District Court, Western District of Tennessee, Civil Docket # 2:07-cv-02175-JPM-dkv, 334 pages.
Transcript Pages: pp. 908-1071, 1085-1102 (Dec. 1-2, 2008), *Spine Solutions, Inc,* v. *Medtronic Sofamor Danek, Inc. et al.*, U.S. District Court, Western District of Tennessee, Civil Docket # 2:07-cv-02175-JPM-dkv, 192 pages.
Viscogliosi et al., "Spine Arthroplasty: Market Potential & Technology Update", Musculoskeletal Research, Nov. 2001, 202 pages.

\* cited by examiner

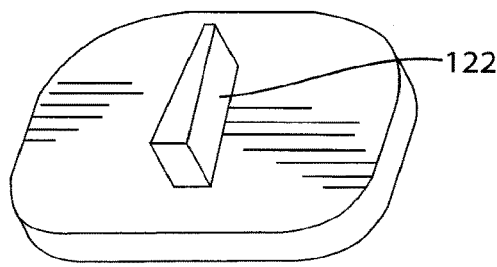
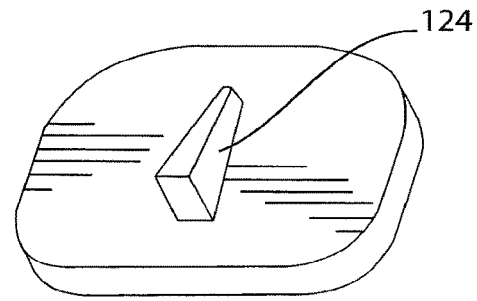
Fig. 25          Fig. 26
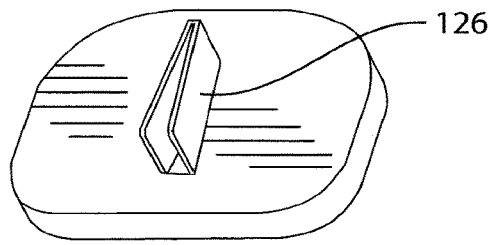
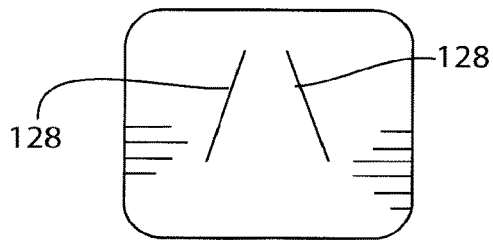
Fig. 27          Fig. 28
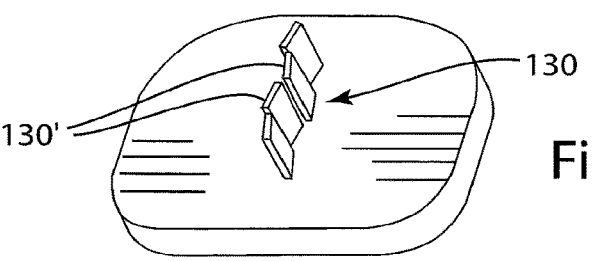
Fig. 29
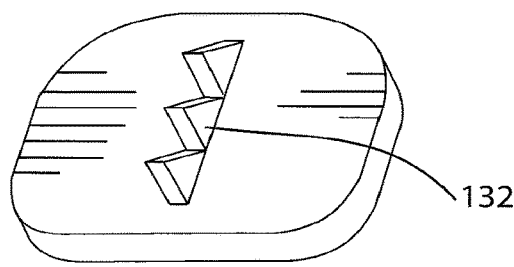
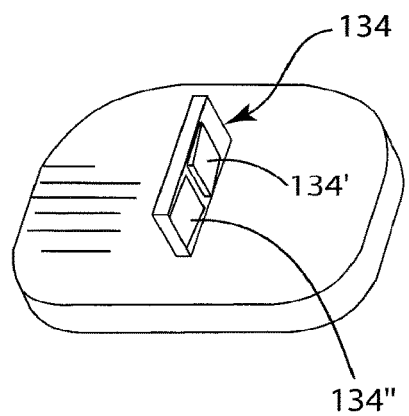
Fig. 30          Fig. 31

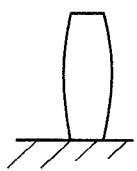 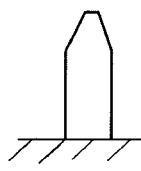 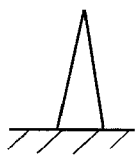 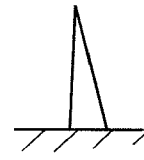
Fig. 32　　Fig. 33　　Fig. 34　　Fig. 35
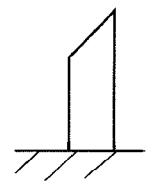 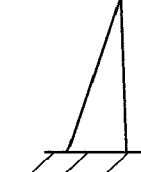 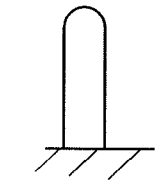 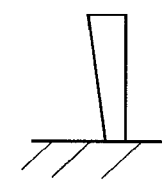
Fig. 36　　Fig. 37　　Fig. 38　　Fig. 39
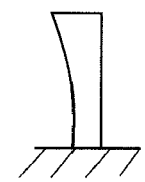 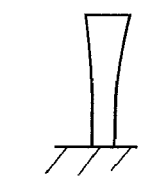 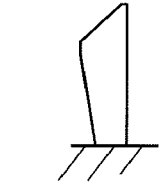 
Fig. 40　　Fig. 41　　Fig. 42　　Fig. 43
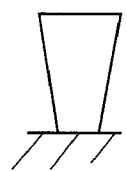 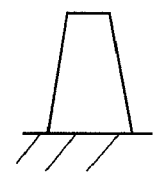 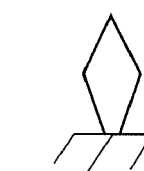 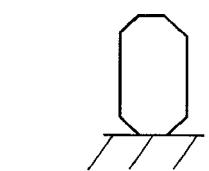
Fig. 44　　Fig. 45　　Fig. 46　　Fig. 47

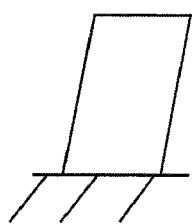 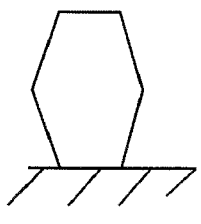 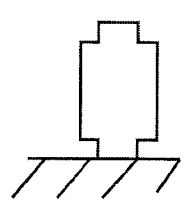 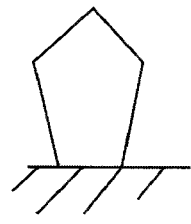
Fig. 48  Fig. 49  Fig. 50  Fig. 51
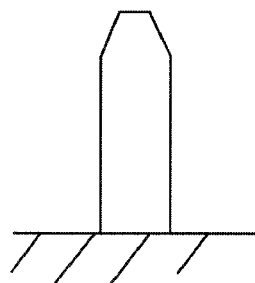 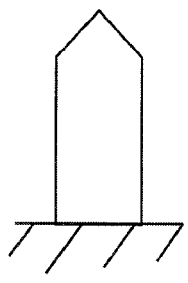 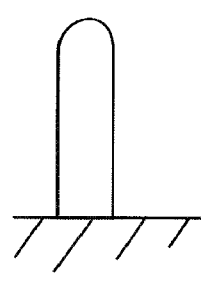 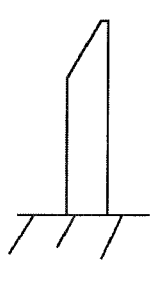
Fig. 52  Fig. 53  Fig. 54  Fig. 55
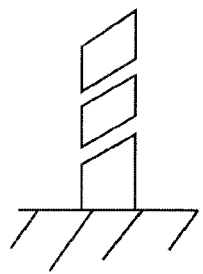 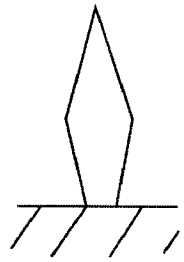 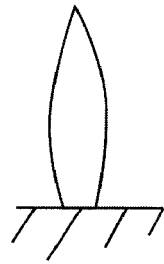
Fig. 56  Fig. 57  Fig. 58

OSCILLATOR

INTERVERTEBRAL IMPLANT WITH KEEL

CROSS REFERENCE TO RELATED APPLICATIONS

This application is a continuation application of U.S. patent application Ser. No. 14/643,287 filed Mar. 10, 2015, now U.S. Pat. No. 9,387,086, which is a continuation application of U.S. patent application Ser. No. 12/375,071 filed Nov. 20, 2009, now U.S. Pat. No. 8,998,990, which is a national stage application of International Patent Application No. PCT/US2007/074218 filed Jul. 24, 2007, which claims priority to U.S. Provisional No. 60/832,595 filed Jul. 24, 2006 and entitled "NEXT GENERATION PRODISC C IMPLANT DESIGN: IP DISCLOSURE" the contents of which are incorporated in their entirety by reference.

BACKGROUND OF THE INVENTION

Historically, when it was necessary to completely remove a disc from between adjacent vertebrae, the conventional procedure was to fuse the adjacent vertebrae together. This "spinal fusion" procedure, which is still in use today, is a widely accepted surgical treatment for symptomatic lumbar and cervical degenerative disc disease.

More recently, there have been important developments in the field of disc replacement, namely disc arthoplasty, which involves the insertion of an artificial intervertebral disc implant into the intervertebral space between adjacent vertebrae. Such a disc implant allows limited universal movement of the adjacent vertebrae with respect to each other. The aim of total disc replacement is to remove pain generation (caused by a degenerated disc), restore anatomy (disc height), and maintain mobility in the functional spinal unit so that the spine remains in an adapted sagittal balance. Sagittal balance is defined as the equilibrium of the trunk with the legs and pelvis to maintain harmonious sagittal curves and thus the damping effect of the spine. In contrast with fusion techniques, total disc replacement preserves mobility in the motion segment and mimics physiologic conditions.

One such intervertebral implant includes an upper part that can communicate with an adjacent vertebrae, a lower part that can communicate with an adjacent vertebrae, and an insert located between these two parts. To provide an anchor to the adjacent vertebrae, each part includes a vertically extending keel. Examples of this type of implant are disclosed in U.S. Pat. No. 5,314,477 (Marnay) and U.S. Pat. No. 7,204,852 (Marnay et al.), which are hereby incorporated by reference.

While this and other known implants represent improvements in the art of artificial intervertebral implants, there exists a continuing need for improvements for these types of implants.

It will also be noted that in order to provide a keel slot in a vertebra, a cutting of the bone needs to be performed. Typically the cut is made by chiseling, drilling or milling. Combinations of these procedures are possible too. However, where a chisel cut is made using a chisel and a mallet, quite high forces are applied in direction of the cut. With drilling, lesser forces are applied, but the drill can slip of or bend during drilling. With milling, a precise cut is made without high forces, but the milling tool needs to have a certain diameter, because otherwise it will brake during milling so milling is not always possible where a long narrow cut is required. Thus, a procedure used to perform narrow cuts without applying high forces is desirable.

Exemplary of such prior art devices and methods are those disclosed in USPA 2004-0215198 (Marnay et al.) and USPA 2006-0064100 Bertagnoli et al.), which are hereby incorporated by reference.

BRIEF SUMMARY OF THE INVENTION

In accordance with the a disclosed embodiment, an intervertebral implant includes two components each having an outer surface for engaging an adjacent vertebra and an inner surface. A keel extends from the outer surface of one component and is designed to be disposed in a slot provided in the adjacent vertebra. This keel extends in a plane which is perpendicular to the outer surface. In one preferred embodiment, there are a pair of keels extending from the other outer surface, which are preferably offset laterally from one another. The pair of keels are preferably symmetrically located on either side of a vertical mid-plane of the outer surface, and are divergent or convergent with respect to each other.

Also in accordance with a disclosed embodiment, an intervertebral implant component of an intervertebral implant includes an outer surface for engaging an adjacent vertebra and an inner surface. A keel extends from the outer surface and is designed to be disposed in a slot provided in the adjacent vertebra. An anterior shelf is also provided at an anterior end of the outer surface, and this anterior shelf extends vertically away from the inner surface in order to help prevent bone growth from the adjacent vertebra towards the inner surface. In accordance with preferred embodiments, the anterior shelf can have a forward surface which is angled, an exterior surface which is polished, and/or a surface treatment which helps prevent bone growth thereon.

Further in accordance with disclosed embodiments, various materials and forms of construction of the component are disclosed. Posterior and/or anterior reductions of the keel are possible for different benefits. The body strength of the vertebra with keel slots on both the superior and inferior surfaces can also be stronger if the keels of the associated components requiring slots are laterally offset. Embodiments of components with modular keels, as well as a variety of advantageous keel shapes (both in horizontal cross section and vertical cross section) are also disclosed.

It will also be appreciated that various combinations of the features disclosed hereafter for a component, and hence for the implant, are also possible as desired.

An instrument for cutting of keel slots with a saw blade, and in particular for cutting multiple slots simultaneously, is also provided.

Other features and advantages of the present invention are stated in or apparent from detailed descriptions of presently preferred embodiments of the inventions found hereinbelow.

BRIEF DESCRIPTION OF THE DRAWINGS

FIGS. 4A-4D illustrate an exemplary embodiment of another spine stabilization device, in which:

FIG. 4B illustrates a partial cutaway view of the spine stabilization device of FIG. 4A;

FIGS. 25-31 are top, back and left side perspective views of implant components with differently shaped keels for better longitudinal retention.

FIGS. 32-51 are front elevation views of different keel shapes.

FIGS. 52-58 are top plan views of different keel shapes.

DETAILED DESCRIPTION OF THE INVENTION

Materials

Figure 1:
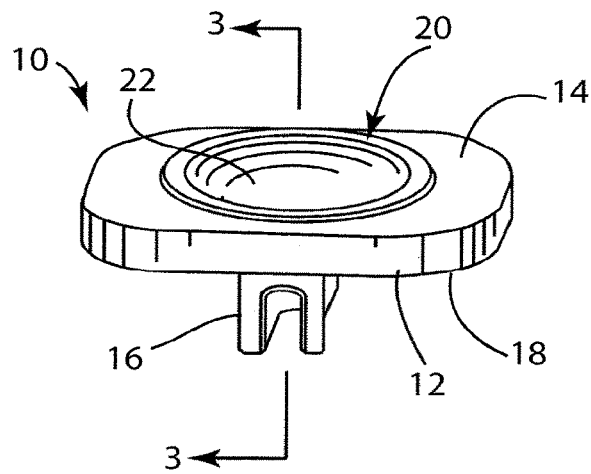
FIG. 1 is a bottom, right and back perspective view of an implant component in accordance with the present invention.

With reference now to the drawings in which like numerals represent like elements throughout the views, a first component 10 of an intervertebral implant for total disc replacement according to the present invention is depicted in FIGS. 1-4. The implant including component 10 is primarily designed for insertion between adjacent vertebrae from an anterior direction. Thus, reference will sometimes be made to anterior and posterior directions for convenience. However, it will be appreciated that insertion from other directions is possible, and hence the referenced directions would thus be similarly changed. In addition, terms such as front/back, forward/rearward, left/right and top/bottom may be used to identify directions as depicted in the figures and/or as the implant is used relative to any insertion direction, even though the "front" may be facing anteriorly or posteriorly depending on the direction of insertion used. Thus, these terms are used for illustration purposes only and not as limiting terms for the invention.

In this embodiment, implant component 10 is formed of an endplate 12 having an outer surface 14 and an integral keel 16 extending outwardly away from outer surface 14. Outer surface 14 is designed to engage an adjacent vertebra, with integral keel 16 then being located in a slot suitably formed in the vertebra (see FIG. 11 for an illustration of a vertebra having a component mounted therein). Component 10 also includes an inner surface 18 in which an insert 20 is securely located. Insert 20 includes in this embodiment a concavity 22 therein, but it will be appreciated that insert 20 could instead have a convexity. Received in concavity 22 will be a mating component of the implant, allowing a ball joint movement of a similar endplate engaging an adjacent vertebra. The similar endplate could have a mating convexity provided thereon, either integrally formed or as an insert (like insert 20); or alternatively the similar endplate could be part of a substantially identical component, and a third component could be interposed between the two components to provide articulation between the facing concavities (or convexities) of the components.

Component 10 is designed to help overcome the problem of artifacts which arises when an MRI is taken of a metal orthopedic medical device such as an intervertebral implant typically having two such components. During spine surgery, MRI is a standard diagnostic tool used to determine the state of the anatomy by visualizing the soft tissue and nerve roots relative to the bony anatomy. However, commonly used metals for orthopedic devices cause MRI artifacts of different degrees. The amount of imaging artifact is reduced as the density of the material and magnetic properties of the material are decreased. For example, the following biomedical materials create imaging artifacts in decreasing order: stainless steel, CoCr alloy, Titanium alloy, ceramics and plastic polymer materials.

The design of component 10 is made to have a reduced amount of imaging artifact, and is thus comprised of two materials: a soft low density material with properties similar to that of the surrounding bone as the main construct foundation, and a harder dense material insert with superior wear properties for the articulating surface areas or parts. In particular, component 10 includes endplate 12 made of a titanium or titanium alloy, and insert 20 made of a material with good articulating properties such as Co—Cr. It will also be noted that insert 20 is reduced to a small area defining the articulating surface of the implant, further helping to reduce the MRI artifact problem.

Figure 2:
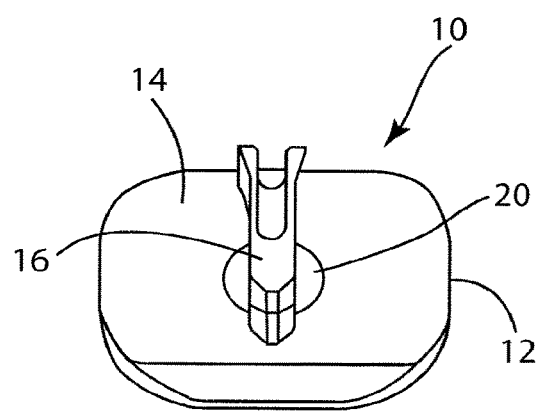
FIG. 2 is a top and front perspective view of the implant component depicted in FIG. 1.
Figure 3:
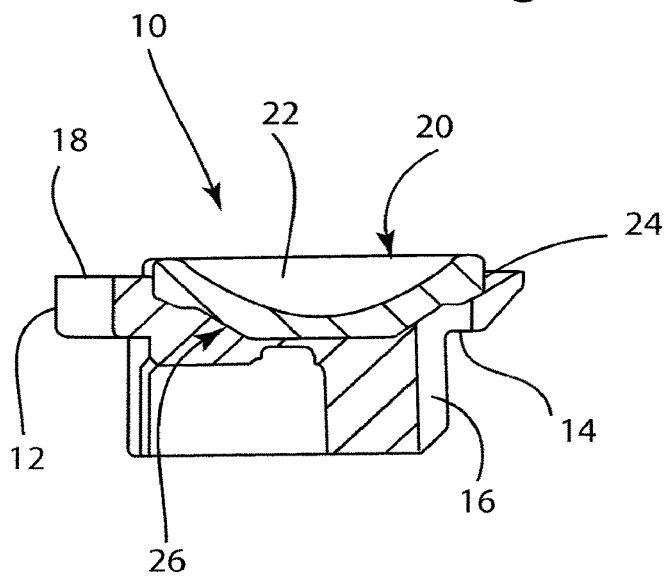
FIG. 3 is cross-sectional side elevational perspective view of the implant component of FIG. 1 taken along the line 3-3 of FIG. 1.
Figure 4:
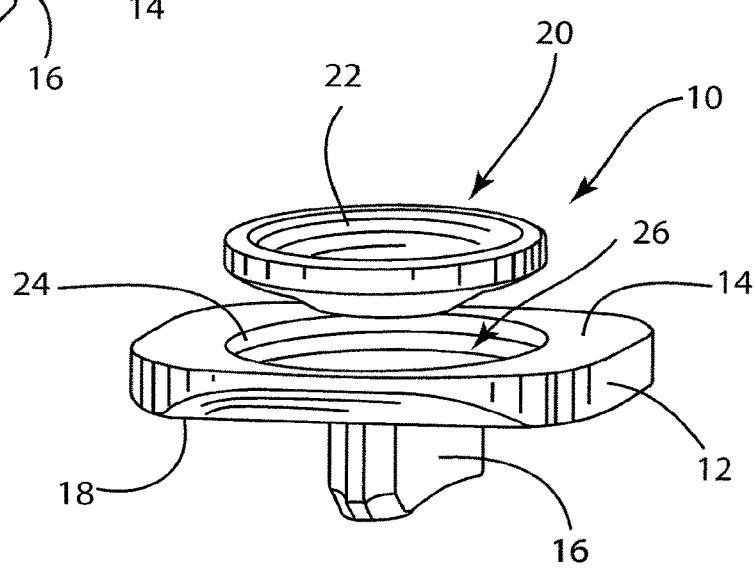
FIG. 4 is an exploded front, bottom, left side perspective view of the implant component of FIG. 1.
Figure 5:
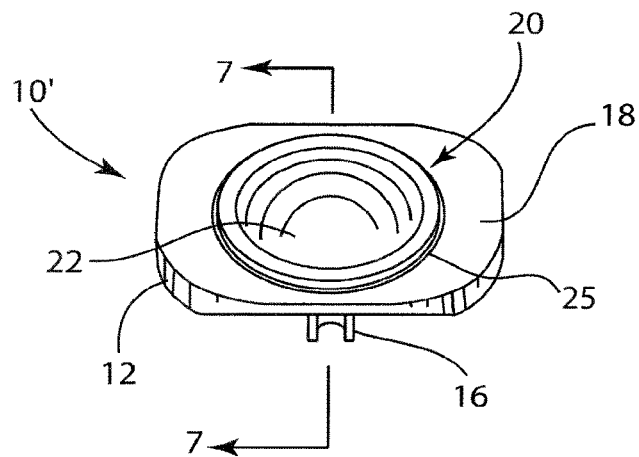
FIG. 5 is a bottom and back perspective view of a second embodiment of an implant component in accordance with the present invention.

Conveniently, insert 20 is a shrink-fit into a cylindrical portion 24 of a receiving and mating cavity 26 of endplate 12 located adjacent inner surface 18, though other ways to secure insert 20 as known in the art are possible (such as a sliding/locking ledge design, threads, adhesives, soldering, pressing, etc.). In this embodiment, it will be appreciated that the receiving cavity 26 of endplate 12 has been optionally designed to pass through outer surface 18, so that a portion of insert 20 is viewable and flat with outer surface 18 as shown in FIG. 2.

Figure 6:
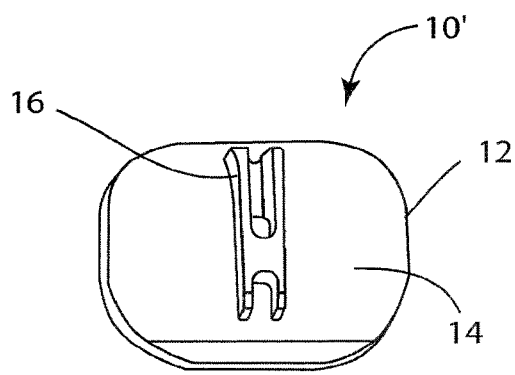
FIG. 6 is a top, front and left side perspective view of the implant component depicted in FIG. 5.
Figure 7:
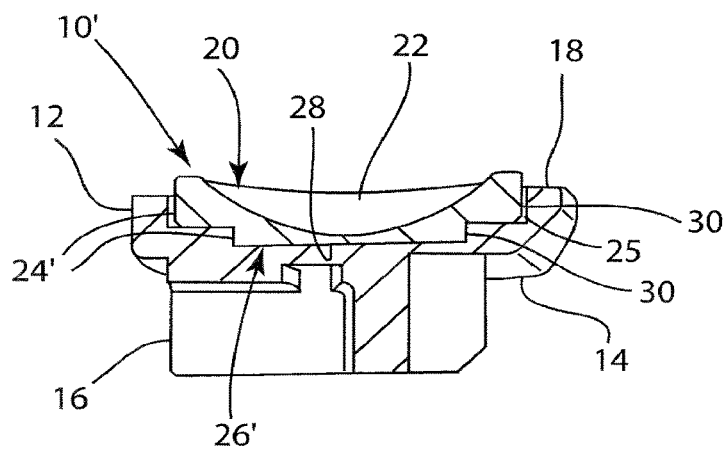
FIG. 7 is cross-sectional side elevational perspective view of the implant component of FIG. 5 taken along the line 7-7 of FIG. 5.
Figure 8:
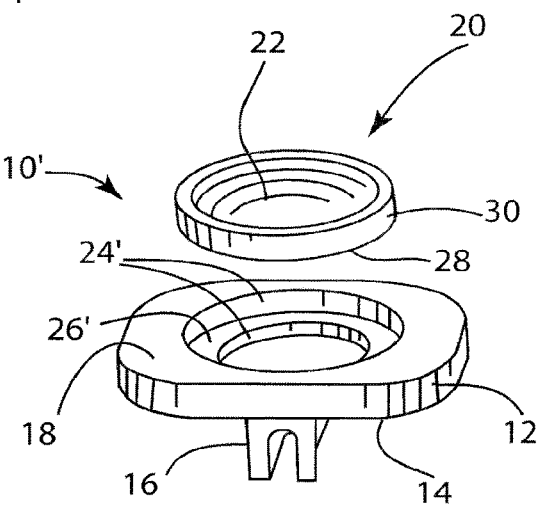
FIG. 8 is an exploded bottom, right and back perspective view of the implant component of FIG. 5.

Depicted in FIGS. 5-8 is an alternative embodiment of a component 10' which is broadly similar to component 10 and whose similar elements will thus be identified with the same reference numerals followed by a prime ('). In this embodiment of component 10', insert 20' has a wide flat bottom 28 (as shown best in FIG. 7, for example) which mates with the similar shape of cavity 26'. This bottom 28 is used to secure insert 20' to endplate 12' by use of a suitable adhesive or the like, while the cylindrical areas 30 on the sides of insert 20' in cavity 26' are slightly spaced from the surrounding metal of cylindrical portion 24' of endplate 12' to create an air channel 25 between the two as shown. It will also be noted that cavity 26' does not extend through to outer surface 14', as shown in FIG. 6.

Other alternatives to the embodiments above could include any number of hard materials and/or surface treatments to be used for the articulating function, such as a ceramic insert, a titanium nitride coated hardened surface, a diamond coated surface such as a DLC (amorphic diamond like carbon), or any other type surface treatment or material for medical use that provides a hardened superior wear surface. A layer of Co—Cr, ceramic, carbon or other biocompatible low-friction material could also be plasma coated and/or sputtered onto the low-density material of an endplate in a position thereof providing the articulating area (ball and/or socket). This layer of material can then be ground, polished, and/or treated to create the desired low-friction, low-wear articulating surfaces.

Alternatives to the titanium base could be PEEK, PEKK, or some other structural polymer, carbon reinforced or other similar composite materials, or any other low density structural biomaterial. A possible alternative could be a pyrolitic carbon implant with a smooth articulating surface and roughened bone contacting surfaces similar to that used in hand and wrist implants.

Posterior Keel Reduction

It has been found that during surgical implantation final seating of the implant endplates has in a few cases proven to be difficult. It is believed that during surgical preparation (typically chiseling, or cutting or drilling) of the keel receiving channel in the vertebral body, not all of the cut bone material is removed but instead some material may be forced to the posterior (or closed) end of the channel by the action of the chisel or the like. This material is then inadvertently left to form an obstruction to the full seating of the keel at the closed end of the channel, resulting in a suboptimal implant position. In order to alleviate this problem, a number of designs are proposed with means designed to accommodate for such excess material, as by a posterior (forward) reduction of the keel. The concept is to create a significantly reduced angled/inclined surface to the forward (or posterior) edge of the keel, more pronounced than the large chamfer at the forward end of the keel such as shown in U.S. Pat. No. 7,204,852 which is designed instead for easier insertion of the keel.

Figure 9:
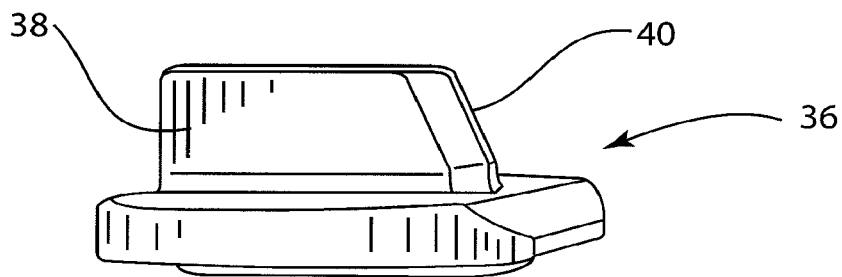
FIG. 9 is a top, front and left side perspective view of an implant component with a pointed keel.

Thus, a means for accommodating excess material in accordance with the present invention is shown in FIG. 9. In this embodiment, component 36 has a keel 38 with a front edge formed as a pointed edge 40 (or knife edge shape). With pointed edge 40, keel 38 can easily cleave through any excess material located in the bottom end of the channel in the vertebra. A similar solution would be to reduce the length of the keel by increasing the distance between the posterior (forward) face of the keel and the posterior (bottom) edge of the component. The depth (bottom) of the clearance cut preparation in the bone of the channel for the keel would then remain the same, but the anterior to posterior (or trailing to leading) length of the keel would be reduced on the posterior (forward or leading) end. Doing this would create added clearance between the bone material left in the channel and the posterior (forward) surface of the keel. FIG. 3G shows a bottom perspective view of the spine stabilization device of FIG. 3E. The inferior plate 26 may also include an opening within which resides a bottom cap 50. This bottom 50 cap may also contain an opening, as shown. This bottom cap 50 may be configured with a curved, round, or chamfered edge so that the inferior plate closely matches the lower endplate of the intervertebral space. Like the other domed cap 40, this domed cap 50 may be eccentric or centric.

Figure 10:
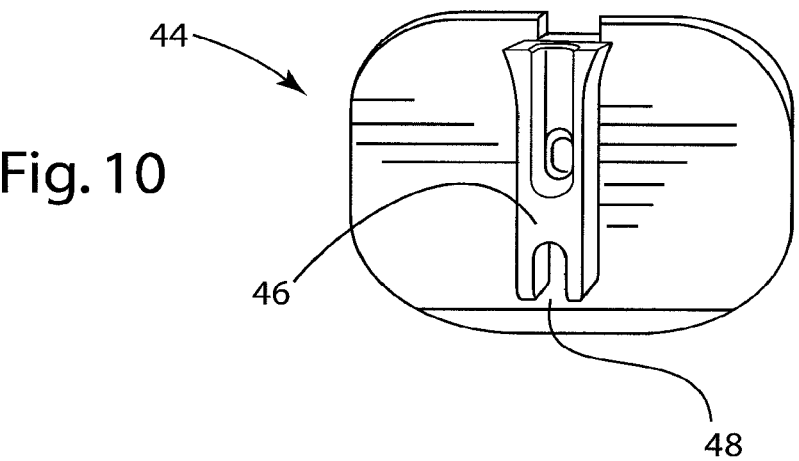
FIG. 10 is a top, back and right side perspective view of an implant component with an H-shaped keel.

Still another means for accommodating excess material is shown in FIG. 10. In this embodiment, component 44 has a keel 46 with a forward U-shape, and preferably an overall an H-shape in plan view. This U-shape can be provided by removing remove material out of the central forward portion of keel 46 so as to create a slot 48 that goes down the front of keel 46. Any obstructive bone material in the channel would fill into the slot 48 and allow keel 46 to fully seat in the formed channel.

Anterior Keel Reduction

Figure 11:
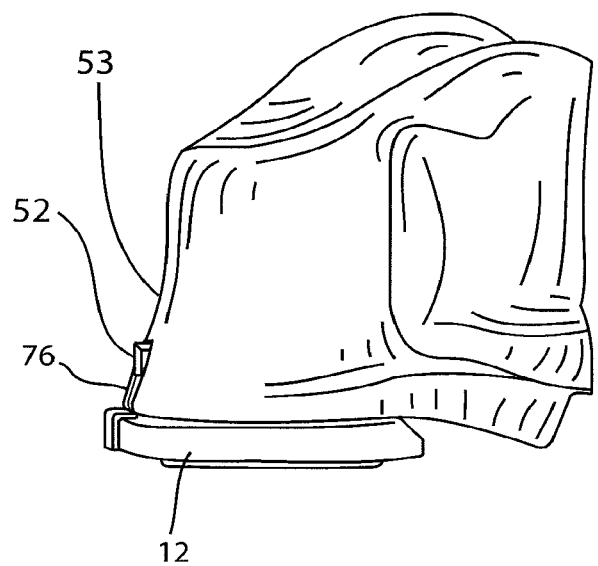
FIG. 11 is a top, back and left side perspective view of an implant component inserted in a vertebra with an anterior corner of the keel exposed.

It has also been found that in rare cases, due to the irregular anatomy of some patients and/or in cases of extreme anterior (rearward) positioning of the implant, an anterior (rearward) top (outer) corner 52 of a keel may be proud or protruding out from the anterior (rearward) surface 54 of the bone as shown in FIG. 11. This exposed metal corner can cause irritation in surrounding tissue. For that reason, a means for slightly reducing the anterior (rearward) corner profile in the keel in the anterior (rearward) end (as well as posterior end, if desired, as noted above) is desirable.

Figure 12:
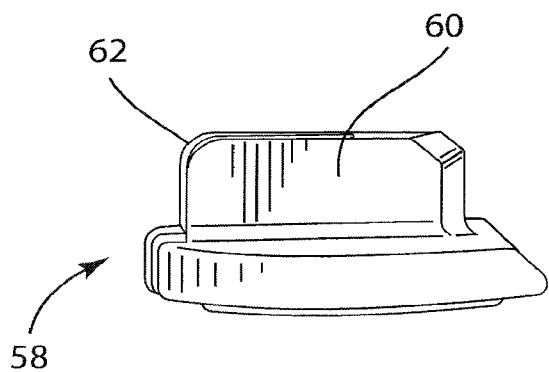
FIG. 12 is a top, back and left side perspective view of an implant component with a keel with a rounded top corner.
Figure 13:
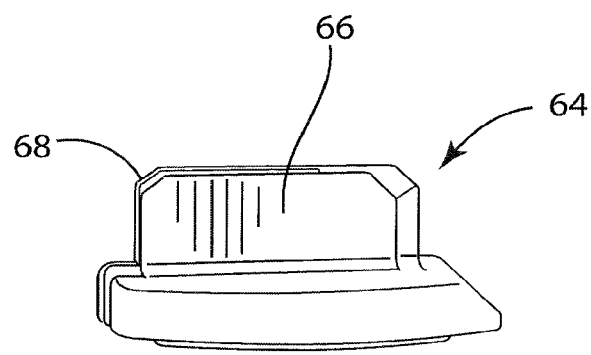
FIG. 13 is a top, back and left side perspective view of an implant component with a keel with a chamfered top corner.

One means for slightly reducing the anterior (rearward) corner profile in the keel at the anterior end is to provide a component 58 with a keel 60 in which the anterior (rearward) corner is reduced by a curved rounded surface 62 as shown in FIG. 12. Another means for slightly reducing the anterior (rearward) corner profile in the keel at the anterior (rearward) end is to provide a component 64 with a keel 66 in which the anterior (rearward) corner is reduced by a chamfer 68 as shown in FIG. 13.

Other embodiments could include an angled surface or other feature to reduce keel material in this area.

Vertebral Body Strength

Figure 14:
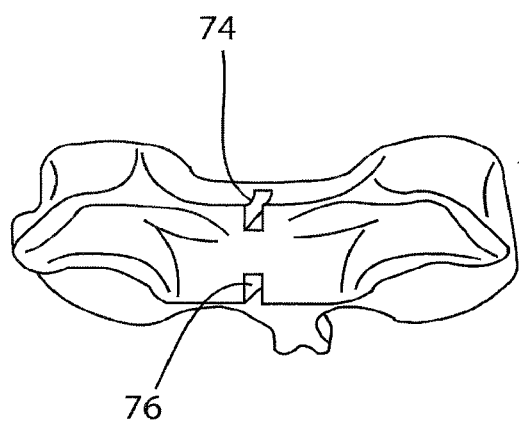
FIG. 14 is a top, back and left side view of a vertebra with symmetrically cut slots for centered keels.

In small or weakened vertebrae, weakening of the bone due to the alignment in the central axis of the spine of keel receiving channels 74 and 76 superior and inferior to vertebra 72 in a multi-level (consecutive) disc replacement case will occur as shown in FIG. 14. This occurrence would leave a much smaller central portion of the bone in vertebra 72, possibly creating a weaker bony construct surrounding the two keels of the two adjacent implants. Thus, it was determined that designs where the keels would be offset in different locations would be desirable for leaving a more intact stronger bone construct.

Figure 15:
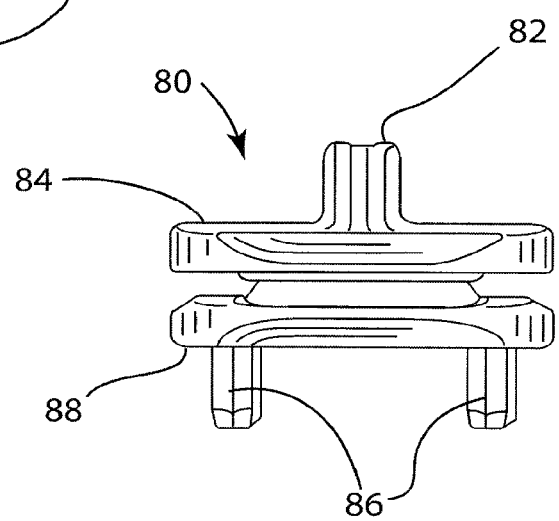
FIG. 15 is a top and front perspective view of mating implant components with two keels of one component offset from the single keel of the other component.
Figure 16:
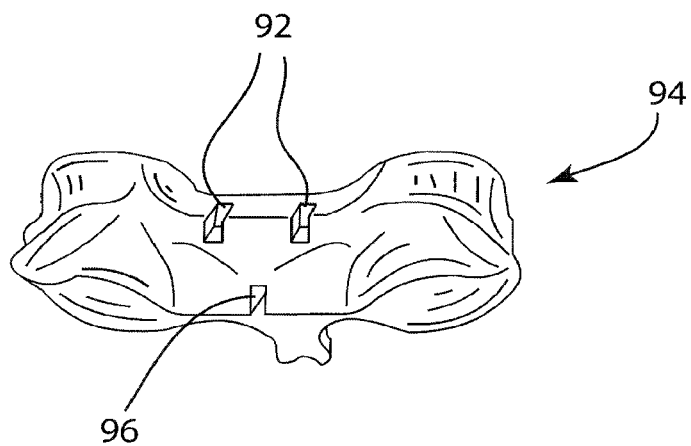
FIG. 16 is top, back and left side view of a vertebra with offset cut slots for the keels of the components depicted in FIG. 15.

One means for offsetting keels in adjacent implants is depicted in FIGS. 15-16. In this embodiment, an implant 80 has a single central keel 80 on one (superior) endplate 82 and double laterally offset keels 84 on the other (inferior) endplate 86. Obviously, the positions of double keels could instead be superior, if desired. However, the desired result of a stronger vertebra is as shown in FIG. 16 where such an implant is used both above and below the depicted vertebra. In particular, there are double keel receiving channels 90 in the superior side of vertebra 92 which are on either side (laterally offset) from single keel receiving channel 94 in the inferior side of vertebra 92—leaving a larger amount of bone in the central area of vertebra 92.

Figure 17:
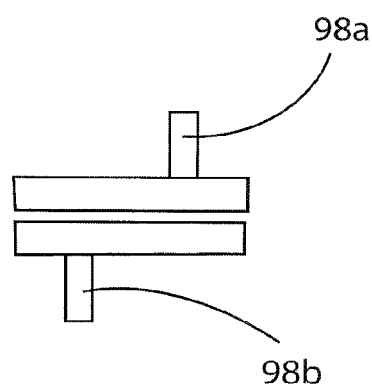
FIG. 17 a front view of mating implant components with one keel of one component offset from the other keel of the other component.

As a variation of this design, the two components of an implant could have oppositely offset keels 98*a* and 98*b* as depicted in FIG. 17.

Figure 18:
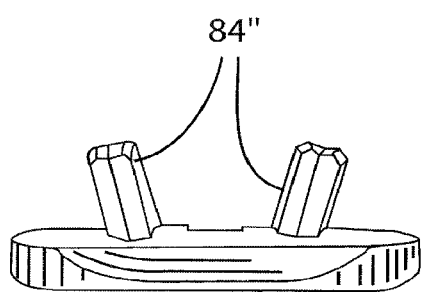
FIG. 18 is a front and top perspective view of an implant component with two keels that are divergent.
Figure 19:
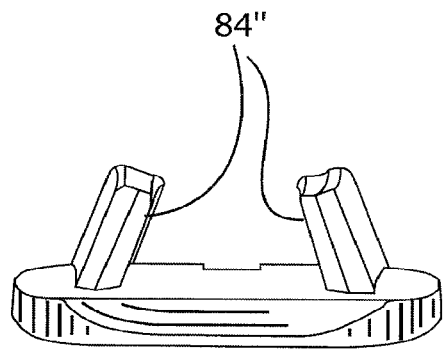
FIG. 19 is a front and top perspective view of an implant component with two keels that are convergent.

Another variations of this design could include embodiments wherein offset keels 84' are divergent at a certain angle as shown in FIG. 18, or offset keels 84" are convergent as shown in FIG. 19. The enhanced benefit of having divergent/convergent keel designs is to prevent loosening of the associated endplate with that type of geometry. The divergent or convergent angles of the keels would add greater resistance to movement in the axial direction and become less likely to be loosened over time. Thus, it will be appreciated that such divergent or convergent keel designs would be beneficial even when not used in consecutive implants; and thus the keels of paired endplates could be both convergent or both divergent, or one convergent and one divergent.

Prevention of Fusion

It has been found that in some cases of total disc arthroplasty in the neck, bone has grown across the implant located in between the vertebral bodies so that the adjacent vertebrae have become fused in spite of the articulating implant provided therebetween. Mostly this problem occurs in the anterior portion of the implant. Therefore, in order to prevent this from happening, a means is added to the implant endplates to retard or stop bone from bridging over the implant.

Figure 20:
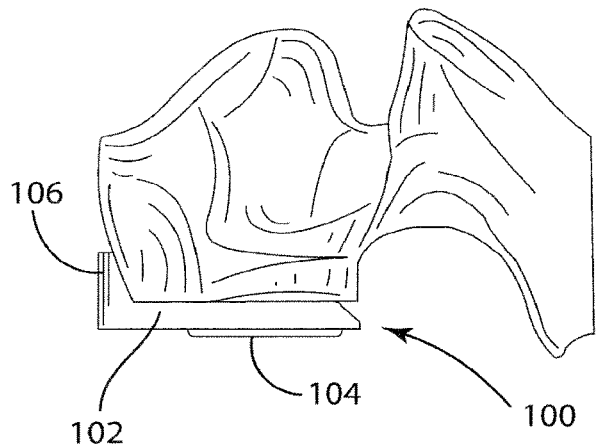
FIG. 20 is a left side view of an implant component having a bone growth retarding plate which is inserted in a vertebra.
Figure 21:
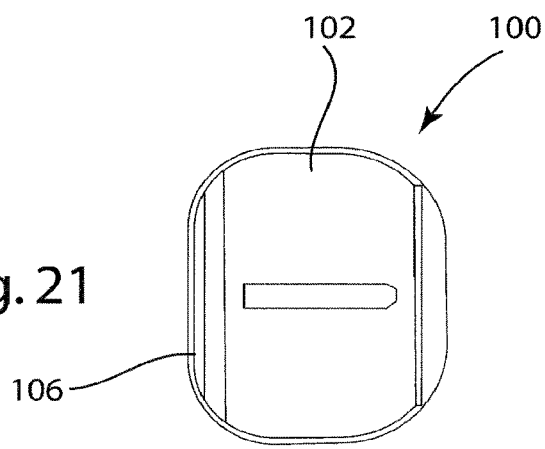
FIG. 21 is a top plan view of the implant component of FIG. 20.

Depicted in FIGS. 20-21 is an implant component 100 having an endplate 102 and insert 104. Provided at the anterior (outer) end of component 102 is a raised plate edge or shelf-like feature 106. The presence of raised edge 106 serves as a means for retarding bone growth/formation between the adjacent vertebrae by its presence and large distance which must then be bridged.

It will also be appreciated that tissue, including bone tissue, tends to grow into and anchor to rough surfaces of titanium implants but does not adhere to certain plastics or other materials. Thus, this raised anterior edge 106 of endplate 104 is preferably polished to a smooth surface finish. Alternatively, the raised anterior edge 106 is treated with a suitable surface coating since bone fusion is usually related to the blood supply and cell formation/cell growth for a given area. For example, an anti-cellular coating could be placed in this area to prevent bone forming and hence undesirable bone fusion. Alternatively, an anti-blood coagulating surface or agent could be integral to raised edge 106. Raised edge 106 could also be designed to hold cement or other material that would contain an anti-coagulant or anti-cellular growth inhibiting agent. The bone cement, implant coating, and/or implant edge fusion block feature could also contain a controlled release anti-inflammatory agent to retard the healing process and thus retard bone growth in that area of undesired fusion.

Modular Keels

Figure 22:
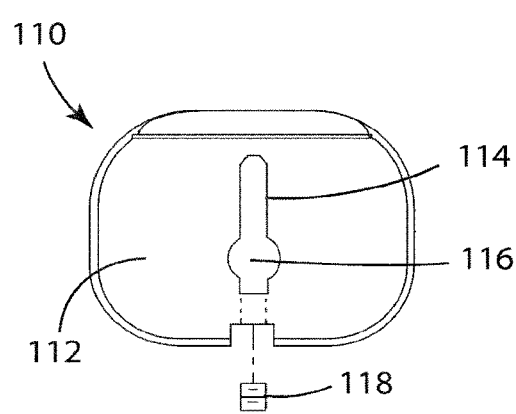
FIGS. 22-24 are top plan views of implant components with different modular keel shapes retainable therein.
Figure 23:
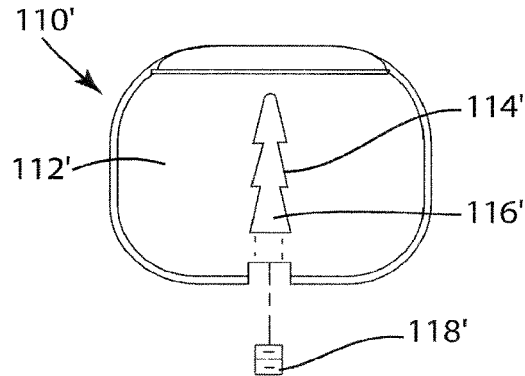
Figure 24:
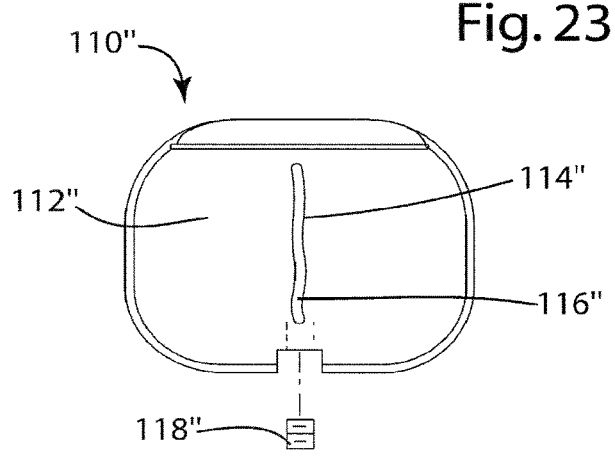

In order to improve fixation of a keel while avoiding removing of some of the vertebra, the keel or other fixation feature of an implant could also be modular as depicted in FIGS. 22-24. With such an embodiment, the endplate is placed into the intervertebral space first; and then the fixation element, such as a keel, is moved through the plate into a mating slot provided in the bone. Finally, that fixation element is then locked to the plate by a suitable mechanical means such as a fastener or set screw. Thus, depicted in FIG. 22 is an implant component 110 having an endplate 112 in which there is a central aperture 114 shaped to matingly receive a keel 116. As shown, set screw 118 is used to secure keel 116 in place in aperture 114 of endplate 112 once keel 116 is located properly. Keel 116 has a "ball" shape at one end, with the vertebra thus having a cutout or slot designed to receive this ball shape. With this shape, keel 116 is more stably held in place longitudinally, without removing so much of the vertebrae.

Other possible keel geometries or configurations are possible, such as the "Xmas Tree" shape of keel 116' of component 110' depicted in FIG. 23, or the snake-shaped keel 116" of component 110" depicted in FIG. 24. It would also be alternatively possible to put the keel in place first, and then attach the endplate to the keel in a similar manner.

Keels Shapes

A variety of different keel shapes are also possible to enhance the ability of the keel to be retained (or not to loosen as easily) in the slot cut into the vertebra. For example, the shape of the keel can be slightly wedged in one dimension (in the forward or insertion direction) as shown by keel 122 in FIG. 25 (or keel 126 in FIG. 27); or in two dimensions as shown by keel 124 in FIG. 26. Typically the wedge shape is regular and symmetrical, but it could also be irregular and unsymmetrical. The wedge shape can go over the whole length of the keel or just in a short section of the keel. The wedge shape of the keel does not need to be solid, and thus could be hollow as shown by keel 126 in FIG. 27. In this embodiment, keel 126 is open from the top, and from the anterior (outer) end; and in another embodiment the keel could also be open from the front (forward end) as shown schematically by keels 128 in FIG. 28. Keel 126 or 128 could also be open from the sides as desired; and it will be thus appreciated that combinations of different openings are also possible.

A keel with steps is also desirable, as shown by keels 130, 132 and 134 shown in respective FIGS. 29, 30 and 31. In the case of keel 130, it consists of respective small parts 130' that are grouped together to build the keel-shape. It will be appreciated that keel 134 also provides special surfaces preventing the backing out by the keel, namely angled out fin or surface 134' and angled in surface 134", even though keel 134 is easy to insert in one (forward) direction as surface 134' has a ramping action in that direction.

While the vertical cross-sectional shape of a keel is typically a simple rectangular shape, the vertical cross-sectional geometry of a keel could also be modified to enhance fixation and/or stability in the bone. This cross section can vary, as it can be symmetrical or asymmetrical. Some examples of different vertical cross-sectional shapes, and combinations of vertical cross-sectional shapes, are shown in the drawings as described hereafter with reference to the noted figures.

FIG. 32: bowed on each side;
FIG. 33: angled asymmetrically on each top side;
FIG. 34: pointed at the top side;
FIG. 35: angled to one side;
FIG. 36: top edge angled;
FIG. 37: right angle triangle shaped;
FIG. 38: round nosed;
FIG. 39: one side inwardly angled;
FIG. 40: one side inwardly bowed;
FIG. 41: both sides inwardly bowed;
FIG. 42: top edge angled to one side which is angled inward;
FIG. 43: angled on each top side, and each side angled inward;
FIG. 44: both sides angled inward;
FIG. 45: both sides angled outward;
FIG. 46: diamond shaped;
FIG. 47: both ends chamfered;
FIG. 48: parallelogram shaped;
FIG. 49: elongated hexagonal shaped;
FIG. 50: both ends stepped at both sides; and
FIG. 51: elongated pentagon shaped.

Also, while the horizontal cross-sectional shape of a keel is also typically a simple rectangular shape, the horizontal cross-sectional geometry of a keel could also be modified to enhance fixation and/or stability in the bone. This cross section can vary, as it can be symmetrical or asymmetrical. Some examples of different horizontal cross-sectional shapes, besides those already mentioned above, and combinations of horizontal cross-sectional shapes, are shown in the drawings as described hereafter with reference to the following figures.

FIG. 52: angled symmetrically toward the leading edge;
FIG. 53: angled symmetrically toward the leading edge to a point;
FIG. 54: rounded leading edge;
FIG. 55: sharply angled to one side leading edge;
FIG. 56: a series of angled leading edges;
FIG. 57: diamond shaped with trailing edge blunted; and
FIG. 58: asymmetrically bowed.

Further, where more than one keel is present on one of the two components the thicknesses of the keels can vary. Some examples of differing thickness keels are shown in the drawings as described hereafter with reference to the following figures.

Figure 59:
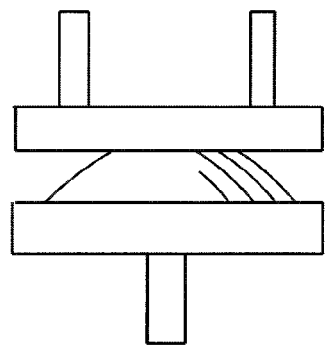
FIGS. 59-61 are schematic front elevation views of mating implant components with different thicknesses of keels.
Figure 60:
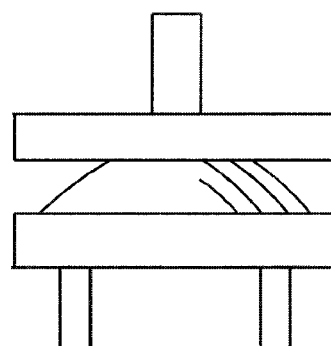
Figure 61:
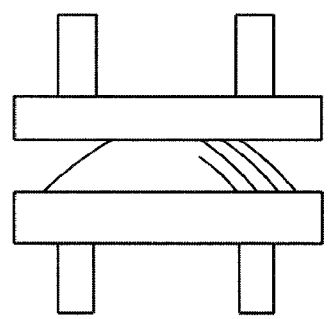

FIG. 59: the top keels have a small and a large thickness, while the bottom keel has an intermediate thickness;
FIG. 60: the bottom keels have a small and an intermediate thickness, while the top keel has a large thickness;
FIG. 61: the top keels have a small and a large thickness, while the bottom keels have a small intermediate thickness and a large intermediate thickness.

Cutting of Dual Keel Slots

As noted above, instruments and methods have been disclosed for cutting keel receiving slots in a vertebra, or in two adjacent vertebrae. Typical of such devices and methods are those shown and described in USPA 2004-0215198 (Marnay et al.) and USPA 2006-0064100 Bertagnoli et al.) which primarily disclose chiseling or burring embodiments.

Figure 62:
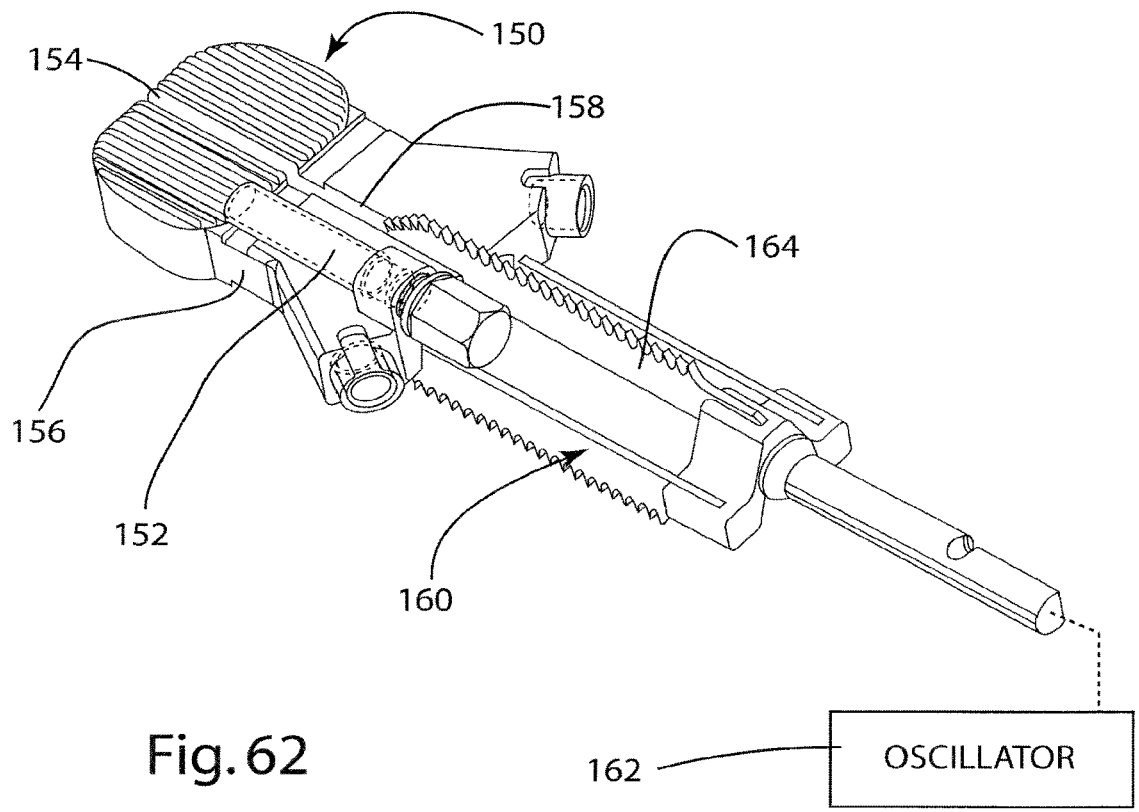
FIG. 62 is a top, back and right side perspective view of an instrument used to cut keel slots.
Figure 63:
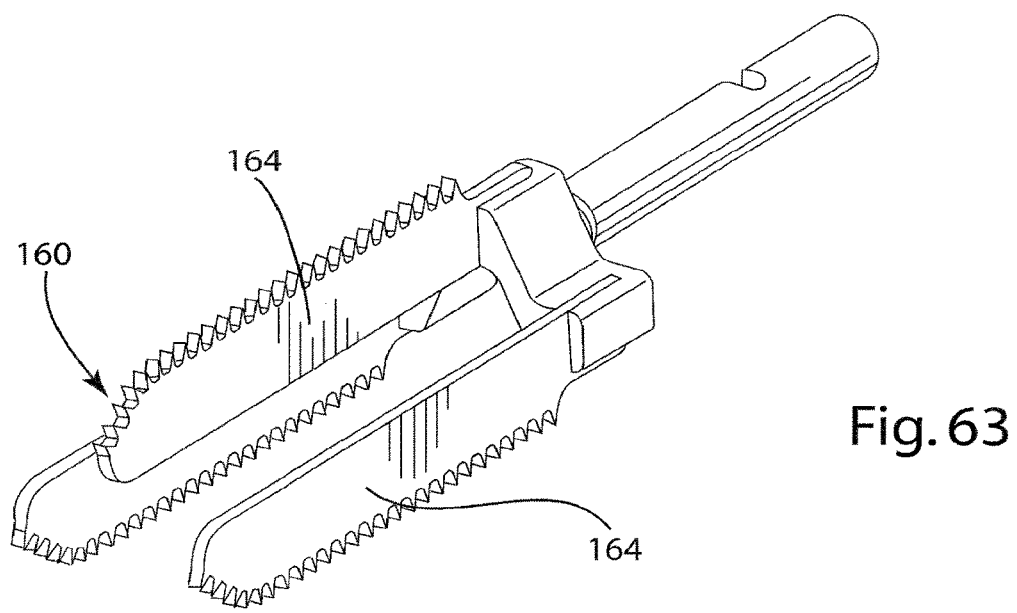
FIG. 63 is a top, front and right side perspective view of the cutting tool depicted in FIG. 62.

Depicted in FIGS. 62-63 is an instrument broadly similar to those disclosed in the above noted published applications, and thus including a trial implant 150 having an adjustable stop 152. The trial implant 150 includes a top slot 154 at the location above which a keel slot is to be cut in a superior (or inferior) vertebra when trial implant 150 is located between two vertebrae. It will be noted that trial implant also has two bottom slots (not shown) similar to top slot 150, but at locations where offset keel slots are to be cut in the inferior vertebra-so that trial implant 150 is thus used to cut the slots for an implant such as disclosed in FIG. 15.

Extending away from trial implant 150 is a guide 156 which is used to guide trial implant into the intervertebral space between two adjacent vertebrae after the disc is removed and to which adjustable stop 152 is threadedly engaged. Guide 156 has slots corresponding to those in trial implant 150, such as top slot 158. Slots 154 and 158 serve to guide saw cutting tool 160 therealong, where cutting tool 160 is rapidly reciprocated by a suitable motor 162 shown schematically and which can take the form of various power tools as known in the art. Rapid reciprocation of saw cutting tool 160 is effective to produce is a reduced impact on the vertebral bone due to the acceleration to mass relationship between cutting tool 160 and the vertebral bone.

It will be appreciated that cutting tool 160 includes three thin saw blades 162 which extend at a proximal edge thereof along slots in guide 156 and trial implant 150, such as slots 158 and 154. At the distal edge, saw blades 162 have suitable cutting teeth 164, which at a leading or forward end form a ramp for easier starting into the vertebra. The insertion depth of cutting blades into the vertebrae is controlled by adjusting the position of adjustable stop 152.

While cutting tool 160 has been shown with three blades, it will be appreciated that only a single blade could be provided to cut each slot individually as needed. It would also be possible to provide a blade more like a chisel but with cutting teeth just at the front. Different interchangeable blades would also be possible, if a narrower or wider, or higher or lower, or deeper or shallower, cut slot was desired. If desired, motor 162 can be dispensed with, and the blade or blades moved by hand with the same guidance. The material of the blades is preferably a suitable metal, but ceramic or plastic blades, or even a diamond cutting blade, would also be possible. If desired or necessary, a coatings to reduce friction could be used with the cutting blades.

Figure 64:
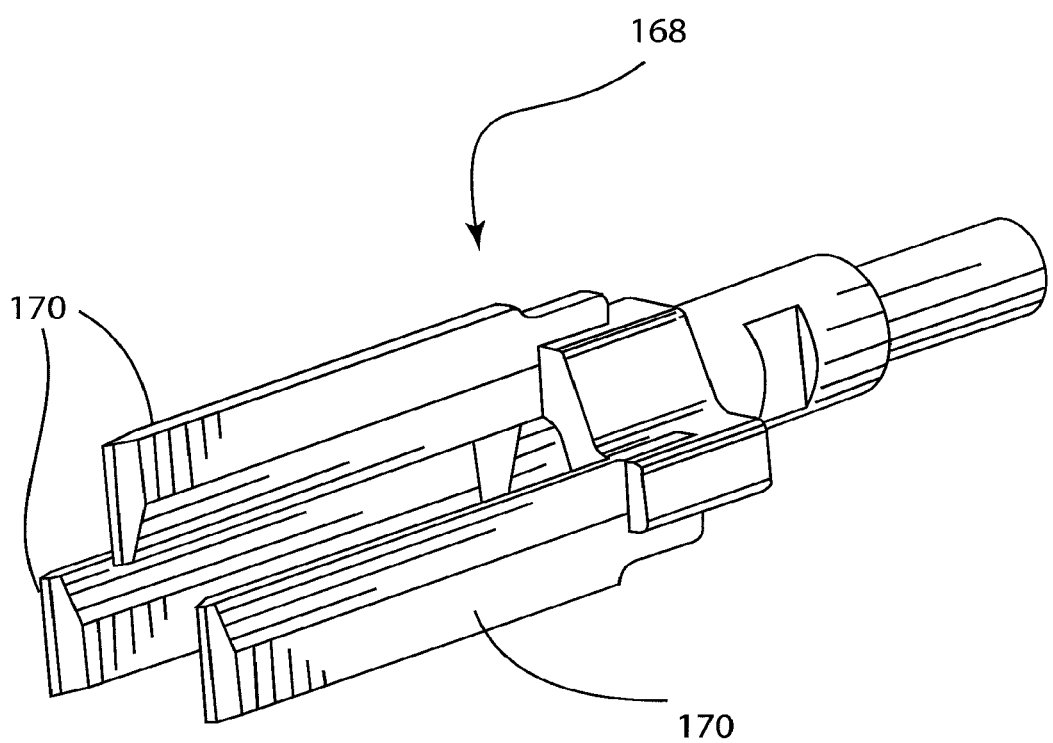
FIG. 64 is a top, front and right side perspective view of an alternative cutting tool for use with the instrument depicted in FIG. 62.

Depicted in FIG. 64 is another cutting tool 168 usable in place of cutting tool 160 and with trial implant 150. Cutting tool 168 includes chisel blades 170 and would thus be used to chisel three slots simultaneously.

Various advantageous features have been described above with respect to various embodiments. Such advantageous features are also considered to be usable together, rather than singly as typically depicted and described.

While the present invention has been described with respect to exemplary embodiments thereof, it will be understood by those of ordinary skill in the art that variations and modifications can be effected within the scope and spirit of the invention. #

What is claimed is:

1. An intervertebral implant for insertion into an intervertebral disc space between two adjacent vertebrae along an insertion direction, the implant comprising:
   a first component having an outer surface for engaging one of the adjacent vertebrae and an inner surface opposite the outer surface, the first component further including a fixation element extending from the outer surface, said fixation element extending in a plane which is substantially perpendicular to said outer surface and having a leading end in the insertion direction and a trailing end opposite the insertion direction, the fixation element defining a recess in the trailing end, wherein the fixation element includes opposed side walls that are substantially parallel to each other and elongate along the insertion direction, wherein the side walls flare away from each along a direction opposite the insertion direction so as to define the trailing end; and a second component having an outer surface for engaging the other of the two adjacent vertebrae and an inner surface opposite the outer surface, and a pair of fixation elements extending from the outer surface, said pair of fixation elements extending on either side of a vertical mid-plane of said outer surface.

2. The intervertebral implant of claim 1, wherein the fixation element of the first component is centered with respect to the pair of fixation elements of the second component.

3. The intervertebral implant of claim 1, wherein each of the pair of fixation elements of the second component is offset from the fixation element of the first component in the lateral direction.

4. The intervertebral implant of claim 1, wherein the fixation element of the first component extends from the outer surface on a vertical mid-plane of the outer surface.

5. The intervertebral implant of claim 1, wherein the fixation element of the first component comprises a keel.

6. The intervertebral implant of claim 1, wherein the pair of fixation elements of the second component comprises a pair of keels.

7. The intervertebral implant of claim 1, further including an insert residing between the first and second components.

8. The intervertebral implant of claim 7, wherein the first component includes a concave surface, and the insert includes a convex surface for engaging the concave surface of the first component.

9. The intervertebral implant of claim 1, wherein the pair of fixation elements each have a second leading end in the insertion direction and a second trailing end opposite the insertion direction, said pair of fixation elements each defining a second recess in the second trailing end.

10. The intervertebral implant of claim 9, wherein the pair of fixation elements each have opposed side walls that are substantially parallel to each other and elongate along the insertion direction, wherein the opposed side walls flare away from each other along a direction opposite the insertion direction so as to define the second trailing end.

11. The intervertebral implant of claim 1 wherein the recess extends through the fixation element in a transverse direction to the insertion direction and terminates at the outer surface of the first component.

12. An intervertebral implant for insertion into an intervertebral disc space between two adjacent vertebrae along an insertion direction, the implant comprising:

a component having an outer surface for engaging one of the adjacent vertebrae and an inner surface opposite the outer surface; and a fixation element extending from the outer surface, said fixation element extending in a plane which is substantially perpendicular to said outer surface and having a leading end in the insertion direction and a trailing end opposite the insertion direction, the fixation element defining a recess in the trailing end, wherein the fixation element includes opposed side walls that are substantially parallel to each other and elongate along the insertion direction, wherein the side walls flare away from each along a direction opposite the insertion direction so as to define the trailing end.

13. The intervertebral implant of claim 12 wherein the recess extends through the fixation element in a transverse direction to the insertion direction and terminates at the outer surface of the first component.

14. The intervertebral implant of claim 12 wherein the fixation element is integral with the component.

15. The intervertebral implant of claim 12, wherein the fixation element extends from the outer surface on a vertical mid-plane of the outer surface.

16. The intervertebral implant of claim 12, wherein the fixation element comprises a keel.

17. An intervertebral implant for insertion into an intervertebral disc space between two adjacent vertebrae along an insertion direction, the implant comprising:

a first component having an outer surface for engaging one of the adjacent vertebrae and an inner surface opposite the outer surface, the first component further including a fixation element extending from the outer surface, said fixation element extending in a plane which is substantially perpendicular to said outer surface and having a leading end in the insertion direction and a trailing end opposite the insertion direction, the fixation element defining a recess in the trailing end; and a second component having an outer surface for engaging the other of the two adjacent vertebrae and an inner surface opposite the outer surface, and a pair of fixation elements extending from the outer surface, said pair of fixation elements extending on either side of a vertical mid-plane of said outer surface, wherein the pair of fixation elements each have a second leading end in the insertion direction and a second trailing end opposite the insertion direction, said pair of fixation elements each defining a second recess in the second trailing end, wherein the pair of fixation elements each have opposed side walls that are substantially parallel to each other and elongate along the insertion direction, wherein the opposed side walls flare away from each other along a direction opposite the insertion direction so as to define the second trailing end.

18. The intervertebral implant of claim 17, wherein the fixation element of the first component is centered with respect to the pair of fixation elements of the second component.

19. The intervertebral implant of claim 17, wherein each of the pair of fixation elements of the second component is offset from the fixation element of the first component in the lateral direction.

20. The intervertebral implant of claim 17, wherein the fixation element of the first component extends from the outer surface on a vertical mid-plane of the outer surface.

21. The intervertebral implant of claim 17, wherein the fixation element of the first component comprises a keel.

22. The intervertebral implant of claim 17, wherein the pair of fixation elements of the second component comprises a pair of keels.

23. The intervertebral implant of claim 17, further including an insert residing between the first and second components.

24. The intervertebral implant of claim 23, wherein the first component includes a concave surface, and the insert includes a convex surface for engaging the concave surface of the first component.

25. The intervertebral implant of claim 17, wherein the recess extends through the fixation element in a transverse direction to the insertion direction and terminates at the outer surface of the first component.

* * * * *